United States Patent
Baden et al.

(10) Patent No.: US 7,202,271 B2
(45) Date of Patent: Apr. 10, 2007

(54) FUSED PENTACYCLIC POLYETHERS

(75) Inventors: Daniel G. Baden, Wilmington, NC (US); William M. Abraham, Miami, FL (US); Andrea J. Bourdelais, Wilmington, NC (US)

(73) Assignee: University of North Carolina, Wilmington, NC (US)

( * ) Notice: Subject to any disclaimer, the term of this patent is extended or adjusted under 35 U.S.C. 154(b) by 22 days.

(21) Appl. No.: 10/945,471

(22) Filed: Sep. 20, 2004

(65) Prior Publication Data

US 2005/0148539 A1 Jul. 7, 2005

Related U.S. Application Data

(60) Provisional application No. 60/504,669, filed on Sep. 19, 2003.

(51) Int. Cl.
- A01N 43/02 (2006.01)
- A61K 31/335 (2006.01)
- C07D 313/00 (2006.01)

(52) U.S. Cl. ...................... 514/450; 549/354
(58) Field of Classification Search ........... 514/450; 549/297, 354
See application file for complete search history.

(56) References Cited

U.S. PATENT DOCUMENTS

| 4,522,811 A | 6/1985 | Eppstein et al. |
| 2005/0124685 A1 | 6/2005 | Baden et al. |
| 2005/0124686 A1 | 6/2005 | Baden et al. |

FOREIGN PATENT DOCUMENTS

| WO | WO 03/016353 | 2/2003 |
| WO | WO 05/027903 | 3/2005 |

OTHER PUBLICATIONS

Kimoto et al., "A new, simple method for measuring mucociliary clearance in guinea-pigs", Pulmonary Pharmacology & Therapeutics, vol. 12, pp. 49-54.*
Craig et al., "Novel mechanistic targets for the treatment of subacute and chronic bronchitis", Current Pharmaceutical Design, vol. 7, pp. 199-212.*
Naumann et al., "P-glycoprotein expression increases ATP release in respiratoty cystic fibrosis cells", Journal of Cystic Fibrosis, vol. 4, pp. 157-168.*
Kuipers et al., "Modification of dendritic cell function as a tool to prevent and treat allergic asthma", vol. 23, pp. 4577-4588.*
Conn et al., "Animal models of pulmonary infection in the compromised host: potential usefulness for studying health effects of inhaled particles", vol. 12, pp. 783-827.*
Alvarez et al., Chem. Rev. 1995, 95:1953-1980.
Backer et al., Harmful Algae, 2003, 2:19-28.
Baden, Int. Rev. Cytol. 1983, 82:99-150.
Baden et al., Toxicon 1981, 19(4):455-463.
Baden et al., Toxicon 1982, 20(5):929-932.
Baden, Brevetoxins, Chemistry, Mechanism of Action, and Methods of Detection, pp. 505-532.
Benson et al., J. of Toxicology and Environ. Health, 1999, 56:345-355.
Berge et al., J. Pharm. Sci. 1977, 66(1):1-19.
Bourdelais et al., Cellular and Molecular Neurogiology (2004), 24(4):553-563.
Cheng, et al., Harmful Algae, 83:1-8.
Dodd et al., Brain Res. 1981, 226(1-2):107-18.
Dravid, Journal of Neurochemistry, 2004, 89:739-749.
Edwards et al., Molecular Brain Research, 1992, 14:64-70.
Gawley et al., Chemistry & Biology Ltd. 1995, 2:533-541.
Gould, Int. J. Pharm. 1986, 33:201-217.
Hardy et al., J Neurochem. 1983, 40(3):608-14.
Jeglitsch, et al., J. of Pharm. & Experimental Therapeutics, 1998, 284(2):515-525.
Keck et al., Tetrahedron Lett. 1987, 28:139-142.
Kirkpatrick, Harmful Algae, 2004, 3:99-115.
Lauredo, et al., Am J. Physiol Lung Cell Mol Physiol, 2004, 286:L734-L740.
LePage et al., Brain Research 2003, 959(1):120-127.
Liu et al., Tetrahedron Lett., 2000, 56(30):5391-5404.
Mall et al., Nature Medicine 2004, 10(5):487-493.
Mende et al., Tetrahedron Lett. 1990, 31(37):5307-5310.
Nicolaou et al., J. Am. Chem. Soc. 1995, 117:1171.
Poli et al., Journal of AOAC International 1995, 78(2):538-42.

(Continued)

Primary Examiner—D. Margaret Seaman
Assistant Examiner—Niloofar Rahmani
(74) Attorney, Agent, or Firm—McDonnell Boehnen Hulbert & Berghoff LLP

(57) ABSTRACT

Disclosed are polycyclic polyether compounds of formula I and pharmaceutical compositions comprising such compounds.

(I)

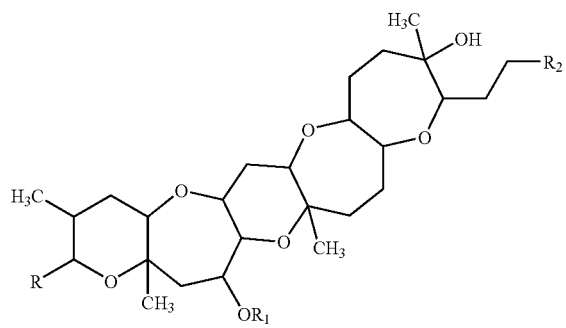

wherein R, $OR_1$, and $R_2$ are as defined herein.

Also disclosed are methods of regulating mucus clearance in a cell, and methods of treating decreased mucus clearance or mucociliary dysfunction.

9 Claims, 5 Drawing Sheets

OTHER PUBLICATIONS

Poli et al., *Molecular Pharmacology* 1986, 30:129-135.
Purkerson-Parker et al., 1999, 20(6): 909-920.
Purkerson-Parker et al., *Chemistry & Biology* 2000, 7(6):385-393.
Rein et al., *Journal of Organic Chemistry* 1994, 59(8):2107-13.
Rein et al., *J. Org. Chem.* 1994, 59:2101-2106.
Trainer et al., *Molec. Pharm.* 1991, 40(6):988-994.
Walsh, *Comparative Biochemistry and Physiology Part B*, 2003, 136:173-182.
Washburn, *Toxicon*, 1994, 32(7):799-805.
Wegner, *Current Pharmaceutical Design*, 2001, 7(3):199-212.
Whitney, *Natural Toxins* 1996, 4:261-270.
International Search Report for related PCT Application No. PCT/US2004/030637.
International Search Report for related PCT Application No. PCT/US2004/030665.
International Search Report for related PCT Application No. PCT/US2004/030535.

* cited by examiner

Effect of Brevenal on PbTx-3 Induced Constriction

- ● PbTx-3
- ▽ PbTx-3 + Brevenal (100 pg/ml)
- ■ PbTx-3 + Brevenal (10 pg/ml)
- ◇ PbTx-3 + Brevenal (3 pg/ml)

Effect of Brevenal on PbTx-2 Induced Constriction

Legend:
- ● PbTx-2
- ▽ PbTx-2 + Brevenal (100 pg/ml)
- ■ PbTx-2 + Brevenal (10 pg/ml)
- ◇ PbTx-2 + Brevenal (3 pg/ml)

X-axis: PbTx-2 (pg/ml)
Y-axis: RL (% change from baseline)

Stimulatory Effects of Toxin Antagonists on TMV

FIGURE 5

FUSED PENTACYCLIC POLYETHERS

This application claims priority from U.S. Provisional Patent Application No. 60/504,669, which was filed Sep. 19, 2003.

FIELD OF THE INVENTION

The invention relates to polycyclic polyether compounds, pharmaceutical compositions comprising the compounds, and methods of treating diseases using the compounds and pharmaceutical compositions. More specifically, the invention relates to a naturally occurring polycyclic polyether compound, "brevenal", isolated from the marine dinoflagellate *K. brevis*, and derivatives thereof. It also relates to pharmaceutical compositions and methods of treating brevetoxin and ciguatoxin poisoning, and diseases that are characterized by decreased mucus clearance and mucociliary dysfunction, comprising the compounds and pharmaceutical compositions.

BACKGROUND

Decreased mucus clearance is a pathologic characteristic of diseases such as cystic fibrosis; chronic obstructive airway disease (also known as chronic obstructive pulmonary disease (COPD)) and asthma. Impaired mucus clearance can also contribute to increased incidence of pulmonary infections and airway obstruction. In particular, cystic fibrosis is characterized by abnormal functioning of the airway epithelial cells. Cystic fibrosis (or "CF") is caused by a defective gene that codes for a $Na^+/Cl^-$ transporter present on the surface of the epithelial cells that line the conducting airways of the lung and other organs. Hundreds of mutations have been identified in this gene, all of which result in defective transport of sodium and chloride by epithelial cells. Cystic fibrosis (CF) is the most common autosomal recessive genetic disease in Caucasians causing premature death in the United States. It is caused by mutations in chromosome 7, which code for the cystic fibrosis transmembrane conductance regulator (CFTR). The CFTR encodes for an apical membrane epithelial protein that function as both a cCAMP-regulated chloride channel and a regulator of the epithelial sodium channel. Defects or absence of the CFTR observed in CF patients can be seen as changes in cilia ultrastructure, sodium and chloride ion transport, and water transport across airway epithelial cells. These changes can result in thickened mucous and decreased mucociliary clearance leading to airway infections. This suggests that CFTR in normal lung tissue may regulate the ENaC by down regulating its conductance of sodium ions across the airway epithelium and decreasing water transport into the cell resulting in less viscous mucous and faster mucociliary clearance.

Current treatment for CF has focused on several different therapies but the most effective treatments to date are compounds that change the viscosity of mucous and treat pulmonary infections that arise when bacteria are trapped in the thickened mucous. Therapies to increase mucociliary clearance generally target two different strategies. The first is to regulate sodium absorption into the apical epithelial cells using sodium channel blockers such as amiloride and its derivatives. By decreasing sodium absorption, fluid transport into the epithelial cells is limited and the surface liquid volume is normalized.

The second strategy is to utilize compounds targeting purinergic receptors (i.e. UTP and INS37217) which activate chloride secretion in airway epithelial cells which in turn decreases sodium absorption and increases surface liquid volume. Purinergic receptors are also thought to regulate mucin secretion and to be involved in activation of ciliary beating. By increasing the ciliary beat frequency, mucous transport would be increased which would clear bacteria and other particles from the lungs more rapidly.

These observations indicate that activation of sodium channels can lead to defects in mucus clearance and bronchoconstriction, both of which are associated with airway diseases, including CF.

If activation of voltage gated sodium channels contributes to lung diseases, then effective modulation of voltage gated sodium channels can be useful in alleviating airway pathologies associated with mucociliary dysfunction, such as asthma, chronic obstructive pulmonary diseases, pulmonary infection (e.g., pneumonia, *Pseudomonas*), and cystic fibrosis. Thus, there is a need for active agents that can modulate water transport across the apical membranes of epithelial cells, these compounds would be are useful in the regulation of mucus clearance, as well as treatment or prevention of conditions or diseases associated with mucociliary dysfunction.

Florida red tides are known to have adverse effects on both marine life and humans. These tides have been linked to large fish kills, marine mammal mortality, and even human illnesses. Human illnesses caused by red tides include respiratory irritation through contact or inhalation and neurotoxic shellfish poisoning (NSP) from consumption of exposed or contaminated seafood (Purkerson-Parker, et al., Chemistry and Biology, 2000, 7: 385–393; Baden, D. G., et al., *Toxicon*, 1982; 20(5):929–932; Baden, D. G., et al., *Int. Rev. Cytol.*, 1983; 82:99–150). Symptoms of NSP include nausea, vomiting, diarrhea, and bronchoconstriction (Purkerson-Parker, et al. 2000). The causative agent in the red tide organisms has been isolated and identified as brevetoxin.

Ciguatera fish poisoning (CFP) is a form of human poisoning caused by the consumption of subtropical and tropical marine fish that have accumulated naturally occurring toxins through their diet. The toxins are known to originate from several dinoflagellate (algae) species that are common to ciguatera endemic regions in the lower latitudes. Marine fish most commonly implicated in ciguatera fish poisoning include groupers, barracudas, snappers, jacks, mackerel, and triggerfish. Many other species of warm-water fish can harbor ciguatera toxins. The occurrence of toxic fish is sporadic, and not all fish of a given species or from a given locality will be toxic.

Initial signs of poisoning occur within six hours after consumption of toxic fish and typically include a combination of gastrointestinal (e.g., nausea, vomiting, and diarrhea), neurological (e.g., intensified paresthesia, arthralgia, myalgia, headache, temperature sensory reversal and acute sensitivity to temperature extremes, vertigo, and muscular weakness), and cardiovascular disorders (e.g., arrhythmia, bradycardia or tachycardia, and reduced blood pressure). Symptoms defined within these general categories vary with the geographic origin of toxic fish. Diagnosis of CFP remains unsatisfactory and is typically based on patient symptoms and recent dietary history.

Ciguatera poisoning is usually self-limiting, and signs of poisoning often subside within several days from onset. However, in severe cases the neurological symptoms are known to persist from weeks to months. In a few isolated cases neurological symptoms have persisted for several years, and in other cases recovered patients have experienced recurrence of neurological symptoms months to years after recovery. Such relapses are most often associated with changes in dietary habits or with consumption of alcohol. There is a low incidence of death resulting from respiratory and cardiovascular failure.

Current treatments for ciguatera fish poisoning are far from satisfactory. Typically intravenous administration of mannitol is used but is normally only effective if it is used in the first 48–72 hours of exposure. The treatment of chronic CFP is usually symptomatic.

CFP and NSP are thought to be induced via binding at a common receptor site on voltage gated sodium channels known as site 5. Binding by brevetoxins or ciguatoxin at site 5 results in massive influx in sodium ions at normal resting potential.

Thus, there is a need for active agents that can act as antagonists for binding of brevetoxins or ciguatoxin to voltage gated sodium channels, which are useful in alleviating the neurological and gastrointestinal effects in persons affected by NSP and CFP.

SUMMARY OF THE INVENTION

We have discovered a fused pentacyclic polyether compound having activity as a brevetoxin antagonist. This compound, Brevenal, is isolated from purified from native sources, such as *K. brevis*, and other red tide organisms. Thus, in one aspect, the invention provides the compound Brevenal which can be represented by the following formula:

In a broad aspect, the invention provides compounds of Formula I:

and pharmaceutically acceptable salts thereof, wherein

R is $C_1$–$C_{12}$ alkyl, $C_2$–$C_{12}$ alkenyl, $C_1$–$C_{12}$ alkyl esters, $C_1$–$C_{12}$ alkyl amides, $C_4$–$C_{12}$ alkenyl esters, $C_1$–$C_{12}$ alkylaryl esters, $C_4$–$C_{12}$ alkenylaryl esters, $C_4$–$C_{12}$ alkenyl amides, $C_1$–$C_{12}$ alkoxy, formyl$C_1$–$C_{12}$alkyl, formyl$C_2$–$C_{12}$alkenyl, alkanoyl$C_1$–$C_{12}$alkyl, alkanoyl$C_2$–$C_{12}$alkenyl, carboxy$C_1$–$C_{12}$alkyl, carboxy$C_2$–$C_{12}$alkenyl, wherein the alkyl and alkenyl groups are optionally substituted with 1–6 substituent groups selected from the group consisting of: $C_3$–$C_{12}$ cycloalkyl, $C_3$–$C_{12}$ heterocyclyl, aryl, heteroaryl, $C_1$–$C_6$ alkyl, $C_1$–$C_6$ alkoxy, halogen, $C_2$–$C_6$ alkenyl, OH, nucleosides, nucleotides, purines, pyrimidines, aromatic esters, aryl esters, cycloalkyl esters, cycloalkenyl esters, purines, or pyrimidines;

$OR_1$ is OH or —O(CO)$CH_3$; and $R_2$ is —CH═CHCH═$CH_2$, —$CH_2$-phenyl, or —$CH_2$-pyridyl, wherein the phenyl and pyridyl groups are optionally substituted at each substitutable position with a group that is independently $C_1$–$C_6$ alkyl, $C_1$–$C_6$ alkoxy, haloalkyl, haloalkoxy, hydroxy, hydroxyalkyl, halogen, —$CO_2H$, $C_1$–$C_6$ alkoxycarbonyl, —C(O)$NH_2$, —C(O)NH($C_1$–$C_6$ alkyl), or —C(O)N($C_1$–$C_6$ alkyl) ($C_1$–$C_6$ alkyl) or pharmaceutically acceptable salts, solvates, esters, amides, hydrates, or combinations thereof.

Brevenal

The compounds of the invention have activity as antagonists of brevetoxins and are therefore useful in treating brevetoxin and ciguatoxin poisoning.

The present invention also provides compounds of Formula I where
R is wherein

Hal is chloro, fluoro, iodo, or bromo;

$R_3$ is selected from H, OH, $NH_2$, halogen, and $NO_2$, and

Y is selected from CH, N, O, and S.

The invention also relates to pharmaceutical compositions comprising a compound of formula I, or a pharmaceutically acceptable salt, hydrate or solvate thereof, in combination with a pharmaceutically acceptable carrier, excipient, solvent, adjuvant or diluent.

The compounds of the invention can also act as antagonists for the class of compounds known as the brevetoxins and ciguatoxin.

The invention further relates to methods of regulating mucus clearance velocity and treating conditions or diseases associated with decreased mucus clearance and mucociliary dysfunction in a subject comprising administering to a subject a compound of formula I or a pharmaceutically acceptable salt, solvate, or hydrate thereof.

The invention also provides methods for treating brevetoxin and ciguatoxin poisoning, comprising administering to a subject a compound of the invention or a pharmaceutically acceptable salt, solvate, or hydrate thereof, in an amount effective to treat brevetoxin or ciguatoxin poisoning. This method of treating brevetoxin and ciguatoxin poisoning can help prevent, treat, reduce the severity of, or delay the onset or progression of symptoms and disease states associated with brevetoxin and ciguatoxin poisoning.

BRIEF DESCRIPTION OF THE FIGURES

FIG. 1 illustrates the effect of brevenal concentrations (3, 10, and 100 pg/mL) on PbTx-3 induced airway constriction in sheep.

FIG. 2 illustrates the effect of brevenal concentrations (3, 10, and 100 pg/mL) on PbTx-2 induced airway constriction in sheep.

Figure 5:
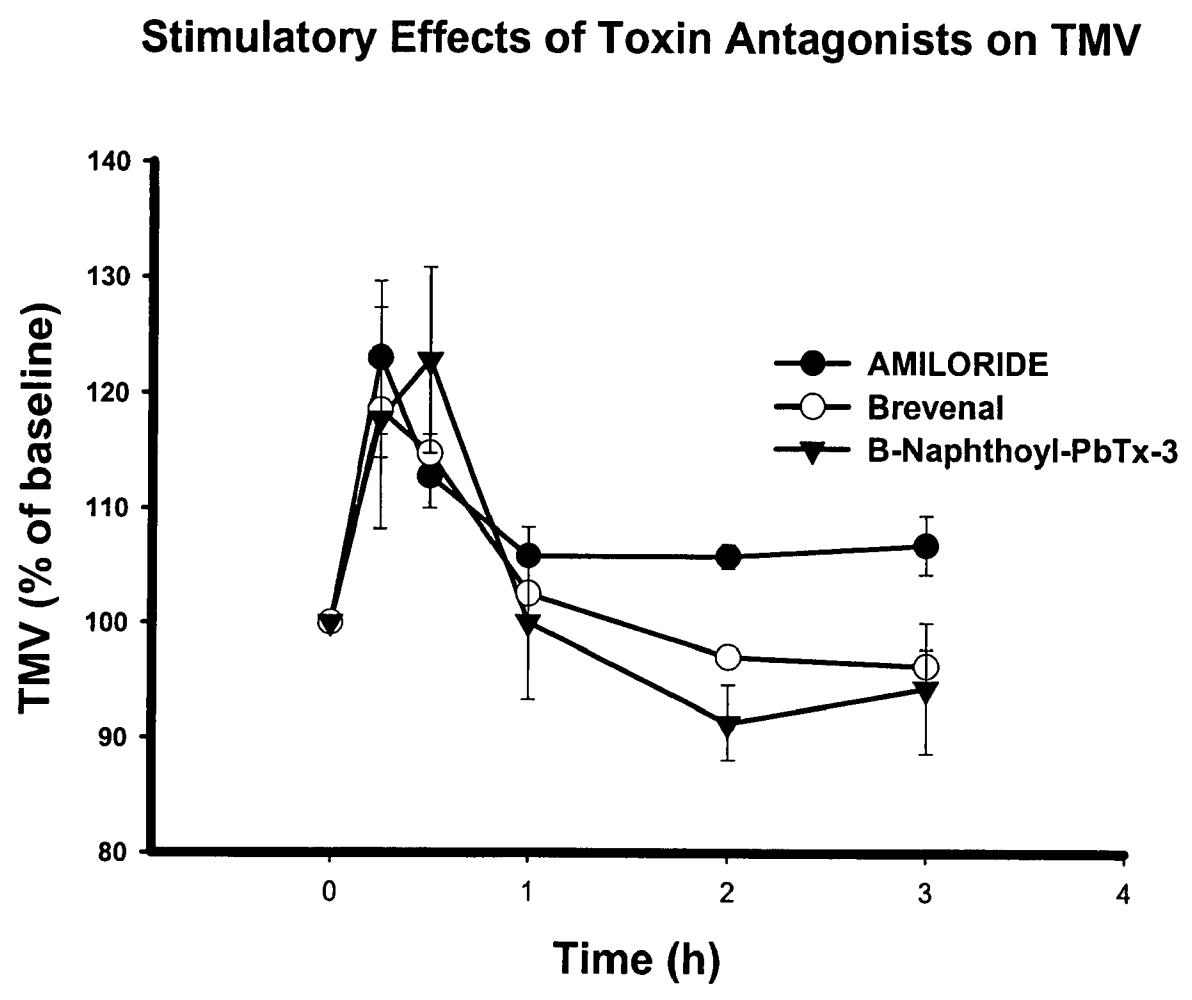

FIG. 5 illustrates the effect of PbTx-3 and PbTx-2 (CONC.10 pg/mL) on tracheal mucus velocity (TMV) in sheep.

DETAILED DESCRIPTION OF THE INVENTION

Definitions

Figure 3:
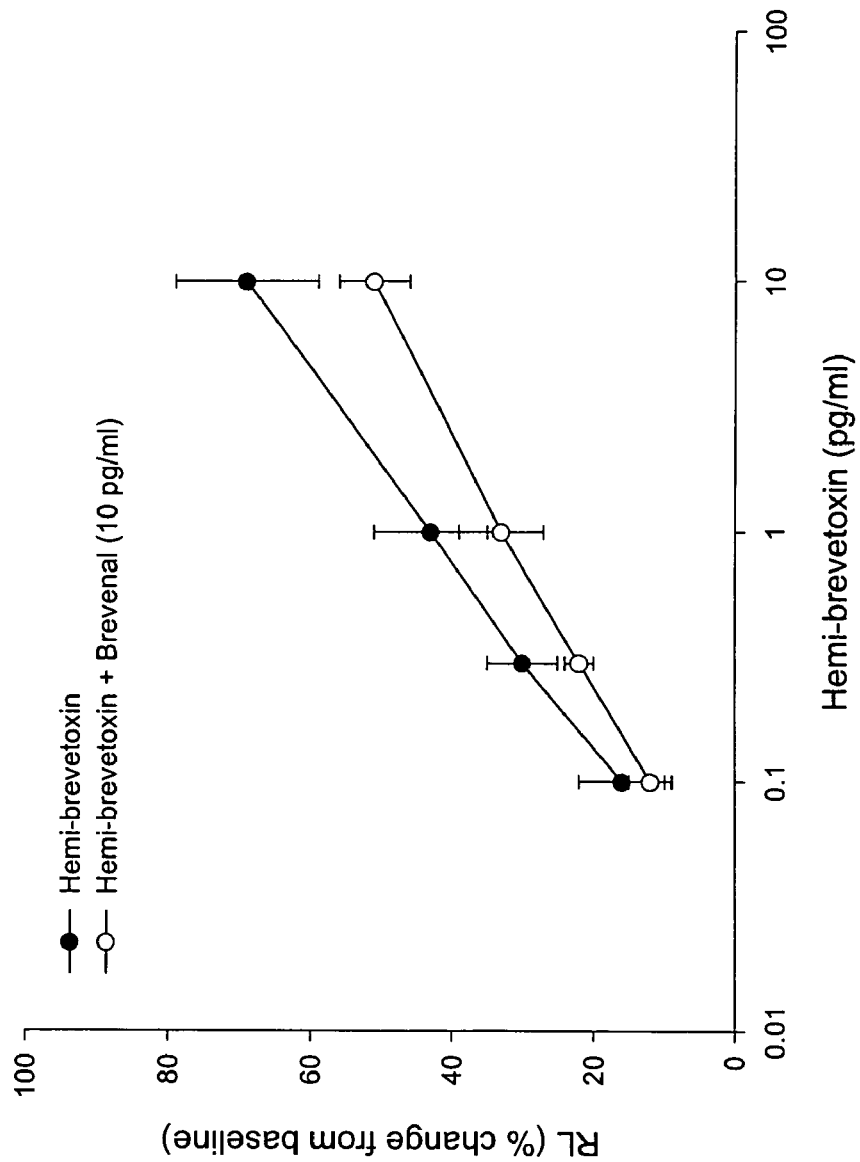
FIG. 3 illustrates the effect of brevenal (10 pg/mL) on hemi-brevetoxin induced airway constriction in sheep.
Figure 4:
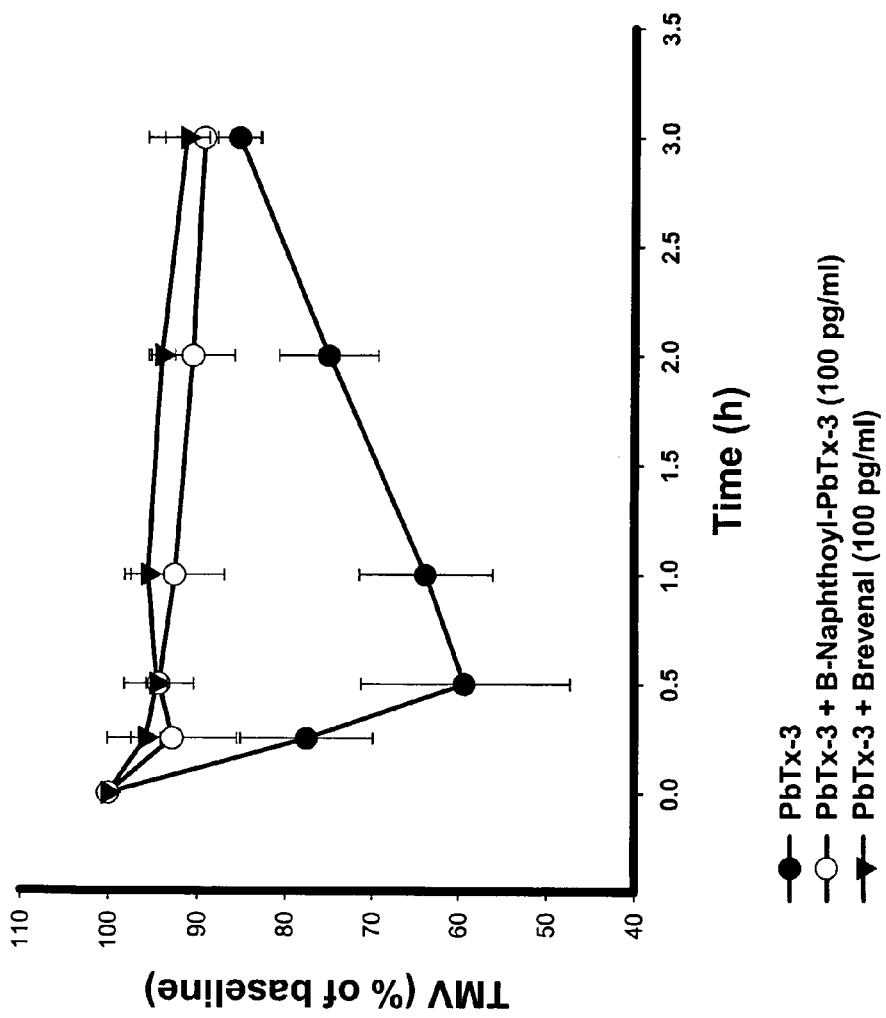
FIG. 4 illustrates the effect of β-naphthoyl-PbTx-3 and brevenal (100 pg/mL) on PbTx-3 induced reduction of tracheal mucus velocity (TMV) in sheep.

Unless defined otherwise, all scientific and technical terms used herein have the same meaning as commonly understood by one of skill in the art to which this invention belongs.

All patents and publications referred to herein are hereby incorporated by reference for all purposes.

A "therapeutically effective" amount is defined as an amount effective to reduce or lessen at least one symptom of the disease being treated or to reduce or delay onset of one or more clinical markers or symptoms of the disease.

As used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

By "alkyl" and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$–$C_{10}$" indicates a maximum of 10 carbons.

By the term "halogen" in the present invention is meant fluorine, bromine, chlorine, and iodine.

"Alkenyl" and "$C_2$–$C_n$ alkenyl" means straight and branched hydrocarbon groups having from 2 to n carbon atoms and from one to four double bonds and includes, for example, ethenyl, propenyl, 1-but-3-enyl, 1-pent-3-enyl, 1-hex-5-enyl, (3E,5E)-4,5-dimethyldeca-3,5-diene and the like.

As used herein, the term "cycloalkyl" refers to saturated carbocyclic groups having three to twelve carbon atoms. The cycloalkyl can be monocyclic, or a polycyclic fused system. Examples of such groups include cyclopropyl, cyclobutyl, cyclopentyl and cyclohexyl. The cycloalkyl groups herein are unsubstituted or, as specified, substituted in one or more substitutable positions with various groups. For example, such cycloalkyl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl or di ($C_1$–$C_6$)alkylamino($C_1$–$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. Preferred aryl groups are optionally substituted with $C_1$–$C_6$ alkyl, $C_1$–$C_6$ alkoxy, halogen, hydroxy, cyano, nitro, amino, mono ($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono($C_1$–$C_6$)alkylamino($C_1$–$C_6$)alkyl or di($C_1$–$C_6$)alkylamino($C_1$–$C_6$)alkyl. Preferred aryl groups are phenyl and naphthyl, each of which is optionally substituted as described above.

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. More preferred heteroaryl groups include oxazolyl, isoxazolyl, pyridyl, pyrimidyl, pyridazinyl, and pyrazinyl. The heteroaryl groups herein are unsubstituted or, as specified, substituted in one or more substitutable positions with various groups. Preferred heteroaryl groups are optionally substituted with $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono ($C_1$–$C_6$)alkylamino($C_1$–$C_6$)alkyl or di($C_1$–$C_6$)alkylamino ($C_1$–$C_6$)alkyl.

By "heterocycle", "heterocycloalkyl" or "heterocyclyl" is meant one or more carbocyclic ring systems of 4-, 5-, 6-, or 7-membered rings which includes fused ring systems of 9–11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, pyrimidine-2,4(1H,3H)-dione, 1H-benzo[d]imidazol-2 (3H)-one tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. More preferred heterocyclic groups include 1H-benzo[d]imidazol-2(3H)-onyl, pyrimidine-2,4(1H,3H)-dionyl, piperidinyl, pyrrolidinyl and piperazinyl. The heterocycle groups herein are unsubstituted or, as specified, substituted in one or more substitutable positions with various groups. Preferred heterocycle groups are optionally substituted with $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono ($C_1$–$C_6$)alkylamino($C_1$–$C_6$)alkyl, di($C_1$–$C_6$)alkylamino ($C_1$–$C_6$)alkyl or =O.

As used herein, the term "arylester" encompasses aryloxycarbonyl and arylcarbonyloxy groups.

As used herein, the term "alkylester" encompasses alkyloxycarbonyl and alkylcarbonyloxy groups. As used herein, alkylcarbonyl carries the same meaning as alkanoyl.

As used herein, the term "alkylamide" encompasses alkylaminocarbonyl groups, dialkylcarbonyl groups, and alkanoylamino groups.

As used herein, the term "alkenylamide" encompasses alkenylaminocarbonyl groups, dialkenylcarbonyl groups, and alkenylcarbonylamino groups.

As used herein, the term "alkenylester" encompasses alkenyloxycarbonyl and alkenylcarbonyloxy groups.

The term alkylarylester as used herein refers to alkyloxycarbonyl and akanoyloxy groups in which the alkyl portion carries an aryl or heteroaryl group.

The term alkenylarylester as used herein refers to alkenyloxycarbonyl and alkenylcarbonyloxy groups in which the alkenyl portion carries an aryl or heteroaryl group.

The phrase "regulating mucous clearance" encompasses "controlling, promoting and/or influencing mucous clearance."

As used herein, the terms "treatment" and "treating" encompass prophylactic administration of the compound or a pharmaceutical composition comprising the compound ("prophylaxis") as well as remedial therapy to reduce or eliminate a disease or disorder mentioned herein. Prophylactic administration is intended for preventing disorders or preventing the recurrence of disorders and may be used to treat a subject that is at risk of having or suffering from one or more disorders mentioned herein. Thus, as used herein, the term "treatment", or a derivative thereof, contemplates partial or complete inhibition of the stated disease state, when an active ingredient of the invention is administered prophylactically or following the onset of the disease state for which such active ingredient of the is administered. "Prophylaxis" refers to administration of the active ingredient(s) to a mammal to protect the mammal from any of the disorders set forth herein, as well as others.

As used herein, the term "subject" encompasses animals, including mammals and fish. Preferably the term refers to mammals such as humans, cattle and horses, more preferably to humans and domestic animals such as cats, dogs, and horses, and most preferably to humans.

In one aspect, the present invention relates to compounds, or pharmaceutically acceptable salts thereof, of Formula (I):

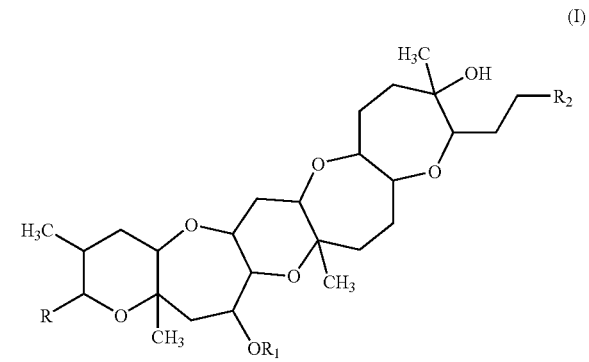

wherein

R is $C_1$–$C_{12}$ alkyl, $C_2$–$C_{12}$ alkenyl, $C_1$–$C_{12}$ alkyl esters, $C_1$–$C_{12}$ alkyl amides, $C_4$–$C_{12}$ alkenyl esters, $C_1$–$C_{12}$ alkylaryl esters, $C_4$–$C_{12}$ alkenylaryl esters, $C_4$–$C_{12}$ alkenyl amides, $C_1$–$C_{12}$ alkoxy, formyl$C_1$–$C_{12}$alkyl, formyl$C_2$–$C_{12}$alkenyl, alkanoyl$C_1$–$C_{12}$alkyl, alkanoyl$C_2$–$C_{12}$alkenyl, carboxy$C_1$–$C_{12}$alkyl, carboxy$C_2$–$C_{12}$alkenyl, wherein the alkyl and alkenyl groups are optionally substituted with 1–6 substituent groups selected from the group consisting of: $C_3$–$C_{12}$ cycloalkyl, $C_3$–$C_{12}$ heterocyclyl, aryl, heteroaryl, $C_1$–$C_6$ alkyl, $C_1$–$C_6$ alkoxy, halogen, $C_2$–$C_6$ alkenyl, OH, nucleosides, nucleotides, purines, pyrimidines, aromatic esters, aryl esters, cycloalkyl esters, cycloalkenyl esters, purines, or pyrimidines;

$OR_1$ is OH or —O(CO)$CH_3$; and $R_2$ is —CH=CHCH=$CH_2$, —$CH_2$-phenyl, or —$CH_2$-pyridyl, wherein the phenyl and pyridyl groups are optionally substituted with 1, 2, or 3 groups that are independently $C_1$–$C_6$ alkyl, $C_1$–$C_6$ alkoxy, haloalkyl, haloalkoxy, hydroxy, hydroxyalkyl, halogen, —$CO_2H$, $C_1$–$C_6$ alkoxycarbonyl, —C(O)$NH_2$, —C(O)NH($C_1$–$C_6$ alkyl), or —C(O)N($C_1$–$C_6$ alkyl) ($C_1$–$C_6$ alkyl).

In another broad aspect, $R_1$ and $R_2$ are as defined above and R is alkyl, halogen, alkenyl, cycloalkyl, aryl, heteroaryl, heterocycle, heterocycloalkyl or heterocyclyl.

In yet another aspect, R is $C_6$–$C_{12}$ alkyl, $C_6$–$C_{12}$ alkyl esters, $C_6$–$C_{12}$ alkyl amides, $C_6$–$C_{12}$ alkylphenyl esters, $C_1$–$C_6$ alkoxy, formyl$C_6$–$C_{12}$alkyl, alkanoyl$C_6$–$C_{12}$alkyl, carboxy$C_6$–$C_{12}$alkyl, wherein the alkyl portions are optionally substituted with 1–4 substituent groups selected from the group consisting of: $C_3$–$C_6$ cycloalkyl, $C_5$–$C_6$ heterocyclyl, penyl, naphthyl, pyridyl, pyrmidyl, pyridazinyl, pyrazinyl, furanyl, thienyl, quinolinyl, indolyl, $C_1$–$C_6$ alkyl, $C_1$–$C_6$ alkoxy, halogen, $C_2$–$C_6$ alkenyl, OH, nucleosides, nucleotides, purines, pyrimidines, phenyl esters, cycloalkyl esters, cycloalkenyl esters, purines, and pyrimidines, wherein each of the cyclic substituents on R is further optionally substituted with up to 5 groups that are independently $C_1$–$C_6$ alkyl, $C_1$–$C_6$ alkoxy, halogen, haloalkyl, haloalkoxy, hydroxy, hydroxy $C_1$–$C_6$ alkyl, $C_1$–$C_4$ alkoxy $C_1$–$C_6$ alkyl, $CO_2H$, C(O)$NH_2$, C(O)NH($C_1$–$C_6$ alkyl), or C(O)N($C_1$–$C_6$ alkyl) ($C_1$–$C_6$ alkyl).

In yet another aspect, R is $C_6$–$C_{12}$ alkenyl, $C_6$–$C_{12}$ alkenyl esters, $C_6$–$C_{12}$ alkenylphenyl esters, $C_6$–$C_{12}$ alkenyl amides, formyl$C_6$–$C_{12}$alkenyl, alkanoyl$C_6$–$C_{12}$alkyl, alkanoyl$C_6$–$C_{12}$alkenyl, carboxy$C_6$–$C_{12}$alkyl, carboxy$C_6$–$C_{12}$alkenyl, wherein the alkenyl groups are optionally substituted with 1–4 substituent groups selected from the group consisting of: $C_3$–$C_6$ cycloalkyl, $C_5$–$C_6$ heterocyclyl, penyl, naphthyl, pyridyl, pyrmidyl, pyridazinyl, pyrazinyl, furanyl, thienyl, quinolinyl, indolyl, $C_1$–$C_6$ alkyl, $C_1$–$C_6$ alkoxy, halogen, $C_2$–$C_6$ alkenyl, OH, nucleosides, nucleotides, purines, pyrimidines, phenyl esters, cycloalkyl esters, cycloalkenyl esters, purines, and pyrimidines, wherein each of the cyclic substituents on R is further optionally substituted with up to 5 groups that are independently $C_1$–$C_6$ alkyl, $C_1$–$C_6$ alkoxy, halogen, haloalkyl, haloalkoxy, hydroxy, hydroxy $C_1$–$C_6$ alkyl, $C_1$–$C_4$ alkoxy $C_1$–$C_6$ alkyl, $CO_2H$, C(O)$NH_2$, C(O)NH($C_1$–$C_6$ alkyl), or C(O)N($C_1$–$C_6$ alkyl) ($C_1$–$C_6$ alkyl).

In still another aspect, $OR_1$ is OH.

In yet still another aspect, $R_2$ is —CH=CHCH=$CH_2$, —$CH_2$-phenyl, or —$CH_2$-pyridyl, wherein the phenyl and pyridyl groups are optionally substituted with 1, 2, or 3 groups that are independently $C_1$–$C_6$ alkyl, $C_1$–$C_6$ alkoxy, haloalkyl, haloalkoxy, hydroxy, hydroxyalkyl, halogen, —$CO_2H$, $C_1$–$C_6$ alkoxycarbonyl, —C(O)$NH_2$, —C(O)NH ($C_1$–$C_6$ alkyl), or —C(O)N($C_1$–$C_6$ alkyl) ($C_1$–$C_6$ alkyl).

In another aspect, R is $C_6$–$C_{12}$ alkenyl substituted with 1, 2, or 3 groups that are independently $C_1$–$C_4$ alkoxy, halogen, —CHO, —OCH$_2$CH$_2$O—, —OCH$_2$CH$_2$CH$_2$O— or OH.

In yet another aspect, R is $C_8$–$C_{12}$ alkenyl substituted with 1, 2, or 3 groups that are independently $C_1$–$C_4$ alkoxy, halogen, —CHO, —OCH$_2$CH$_2$O—, —OCH$_2$CH$_2$CH$_2$O— or OH.

In still yet another aspect, R is $C_9$–$C_{10}$ alkenyl substituted with 1, 2, or 3 groups that are independently $C_1$–$C_4$ alkoxy, —CHO, —OCH$_2$CH$_2$O—, —OCH$_2$CH$_2$CH$_2$O— or OH. In one aspect, when R is substituted with two $C_1$–$C_4$ alkoxy groups, they are the same. Still more preferably, when the two $C_1$–$C_4$ alkoxy groups are the same, they are attached to the same carbon, thereby forming an acetal.

In still another aspect, R is

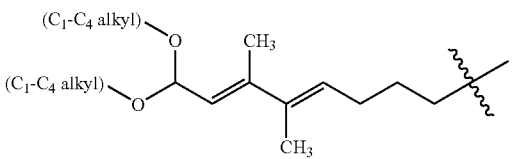

In yet another aspect, R is

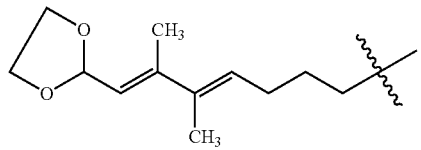

In still another aspect, R is

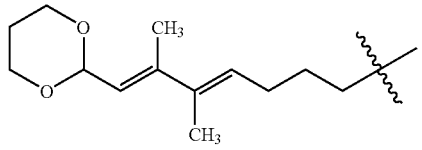

In another aspect, R is

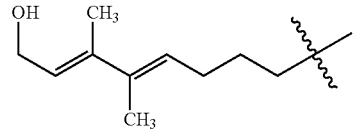

In another embodiment of this aspect, the compound is of Formula (I), wherein R is
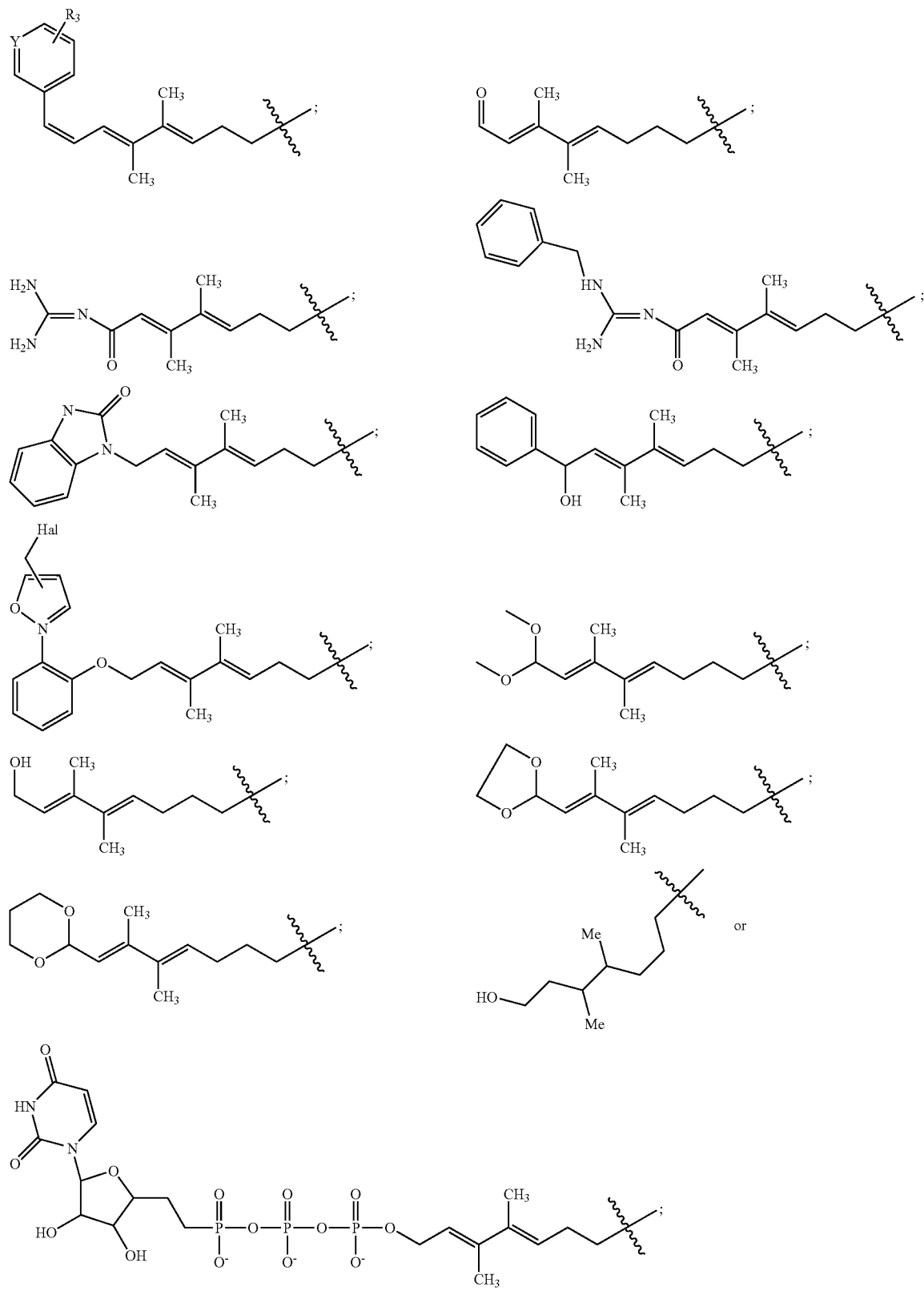

wherein

Hal is chloro, fluoro, iodo, or bromo;

$R_3$ is selected from H, OH, $NH_2$, halogen, and $NO_2$, and Y is selected from CH, N, O, and S.

In another aspect, $R_2$ is —CH=CHCH=$CH_2$.

In a preferred embodiment, $R_2$ in the compound of Formula (I) is —CH=CHCH=$CH_2$ in cis conformation.

In a preferred embodiment, $R_2$ in the compound of Formula (I) is —CH=CHCH=$CH_2$ in cis conformation, and R is a $C_2$–$C_{12}$ alkenyl comprising a diene.

In a more preferred embodiment, $R_2$ in the compound of Formula (I) is —CH=CHCH=$CH_2$ in cis conformation, and R is a $C_2$–$C_{12}$ alkenyl comprising a diene, in trans conformation.

In another embodiment, $R_2$ in the compound of Formula (I) is CH=CHCH=$CH_2$ in the trans conformation, and R is a $C_8$–$C_{12}$ alkenyl comprising a diene, in trans conformation.

In another embodiment, $R_2$ is —$CH_2$-phenyl, or —$CH_2$-pyridyl, wherein the phenyl and pyridyl groups are optionally substituted with 1, 2, or 3 groups that are independently $C_1$–$C_6$ alkyl, $C_1$–$C_6$ alkoxy, $CF_3$, $OCF_3$, hydroxy, hydroxy $C_1$–$C_6$ alkyl, halogen, —$CO_2H$, $C_1$–$C_6$ alkoxycarbonyl, —C(O)$NH_2$, —C(O)NH($C_1$–$C_6$ alkyl), or —C(O)N($C_1$–$C_6$ alkyl)($C_1$–$C_6$ alkyl)

In another embodiment, $R_2$ is —CH=CHCH=$CH_2$. In still another embodiment, $R_2$ is

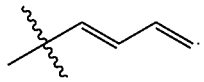

In yet another embodiment, $R_2$ is

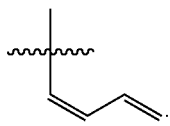

In yet another embodiment, R is

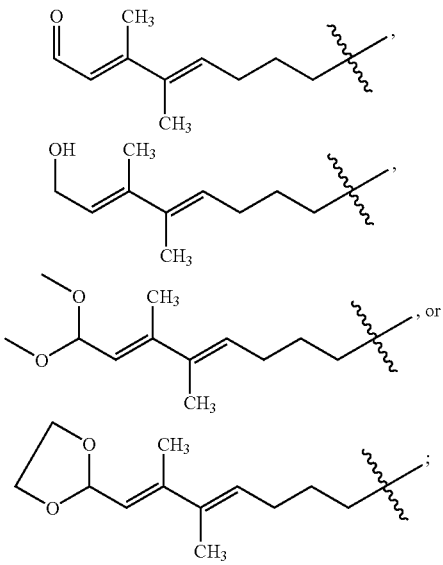

and
$R_2$ is

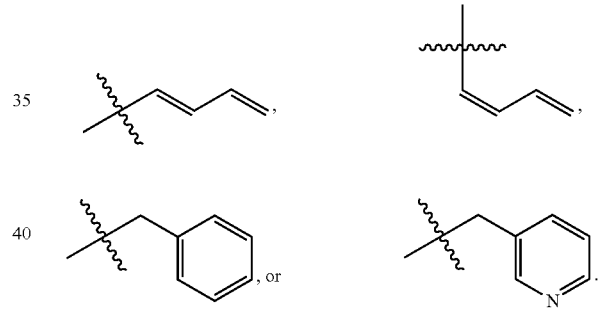

In another embodiment R and $R_2$ are as defined above and $R_1$ is H.

In another preferred embodiment, the compound of Formula (I) is:

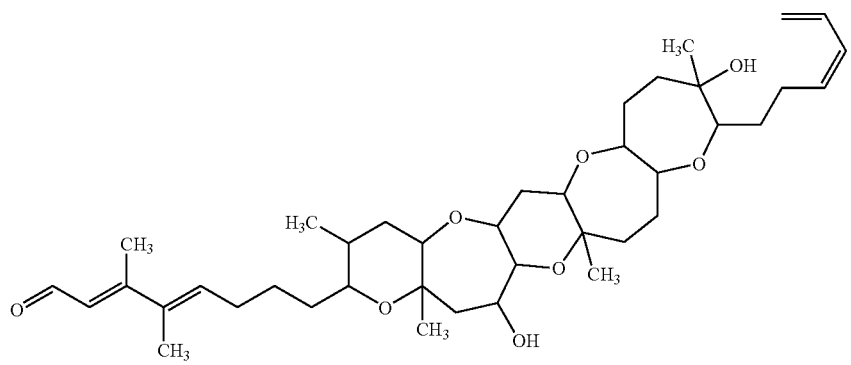

In another preferred embodiment, the compound of Formula (I) is:
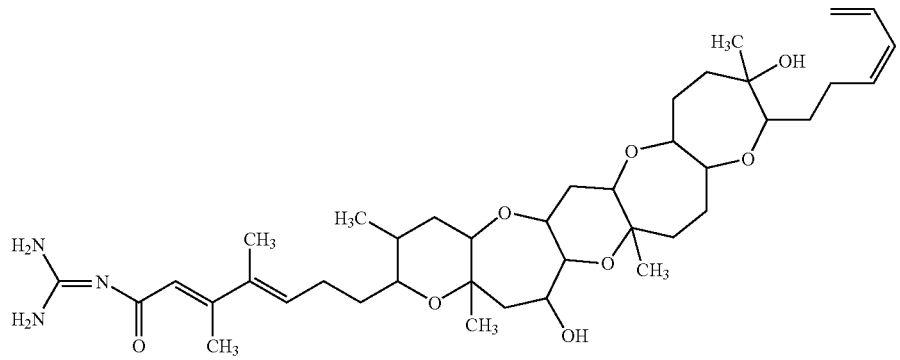
In another preferred embodiment, the compound of Formula (I) is:
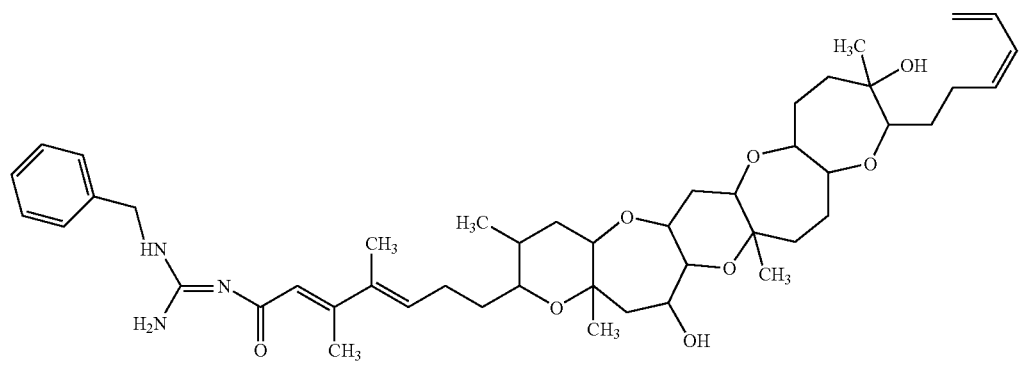
In another preferred embodiment, the compound of Formula (I) is:
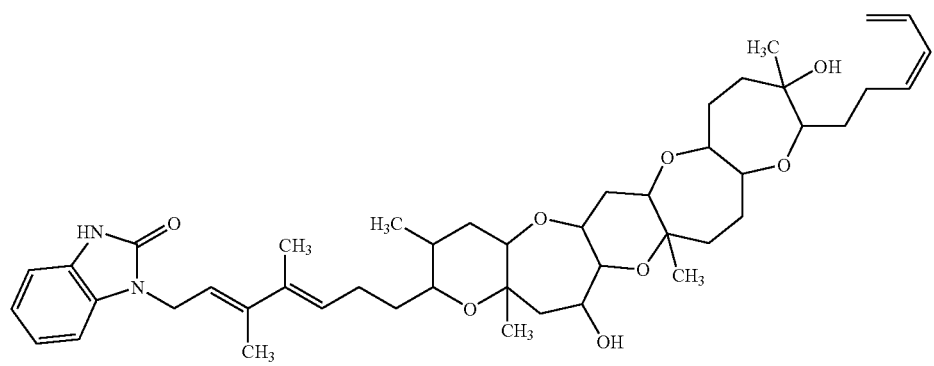

In another preferred embodiment, the compound of Formula (I) is:
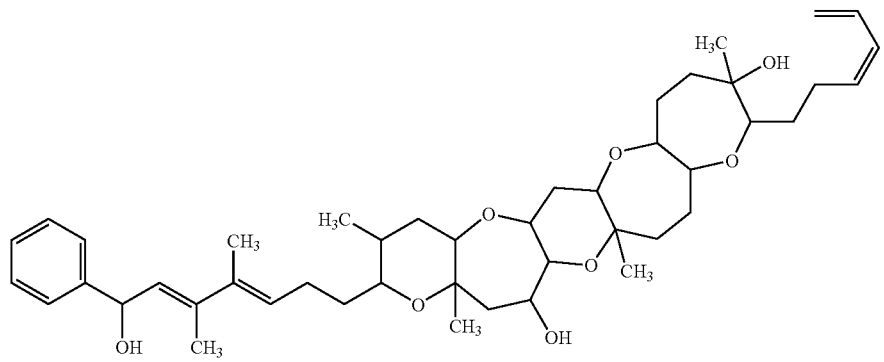
In another preferred embodiment, the compound of Formula (I) is:
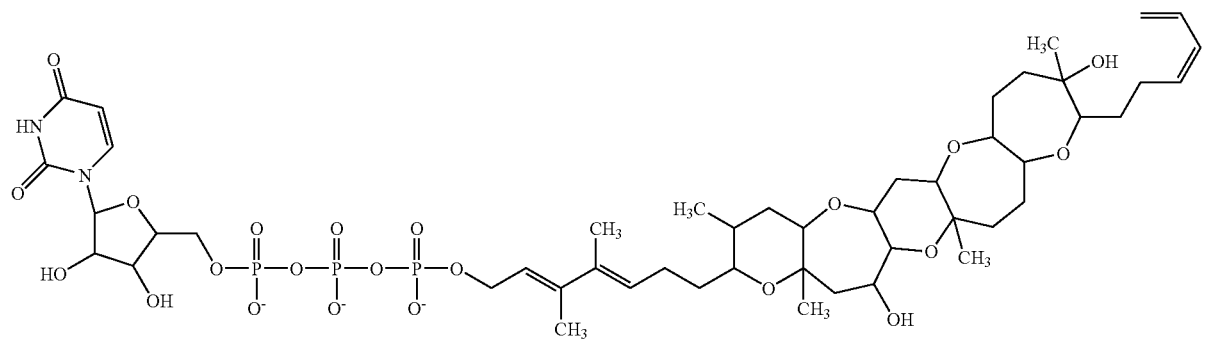
In another preferred embodiment, the compound of Formula (I) is:
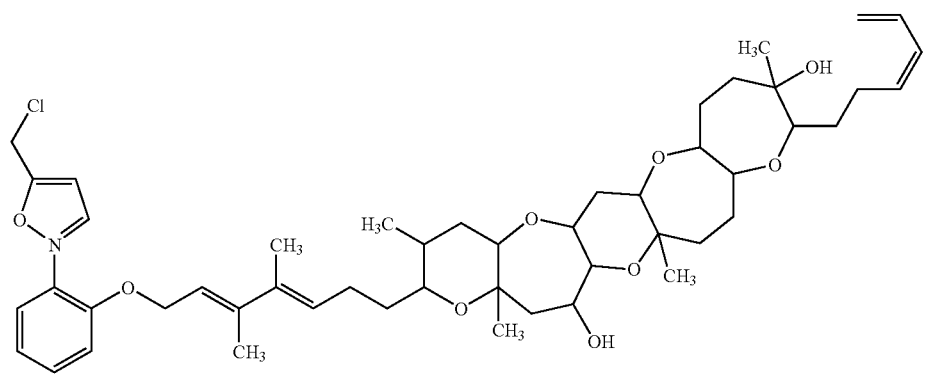

In another preferred embodiment, the compound of Formula (I) is:
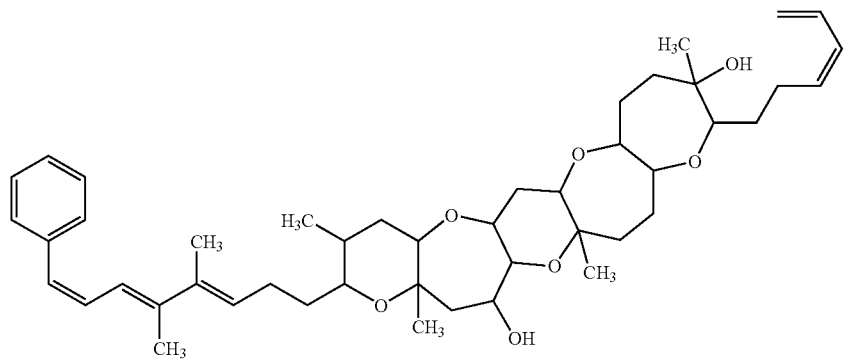
In another preferred embodiment, the compound of Formula (I) is:
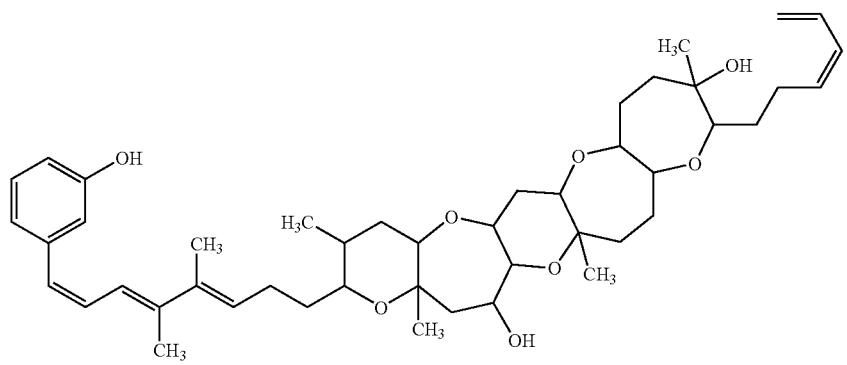
In another preferred embodiment, the compound of Formula (I) is:
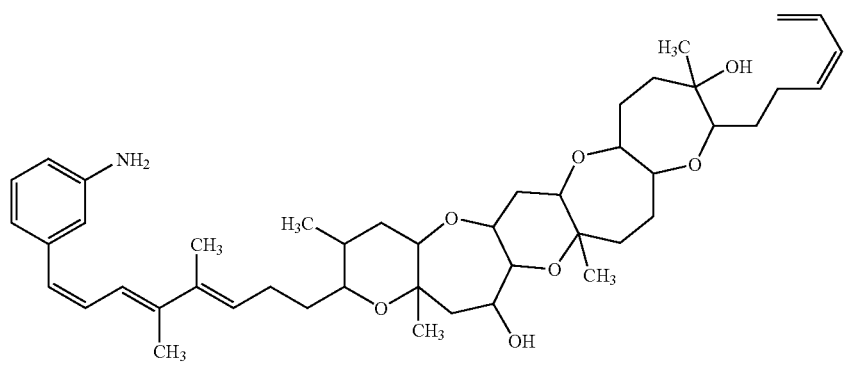

In another preferred embodiment, the compound of Formula (I) is:
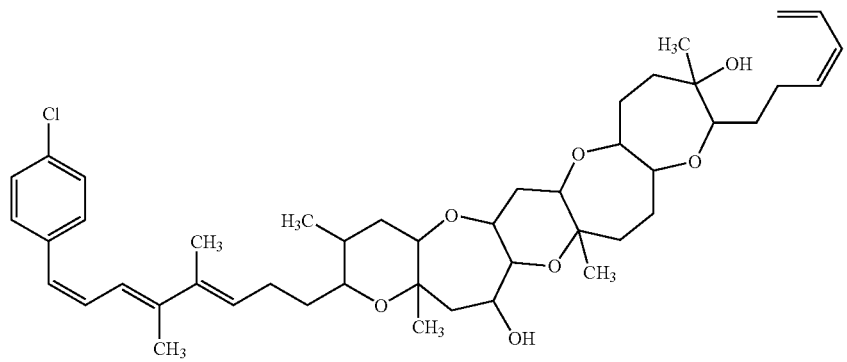
In another preferred embodiment, the compound of Formula (I) is:
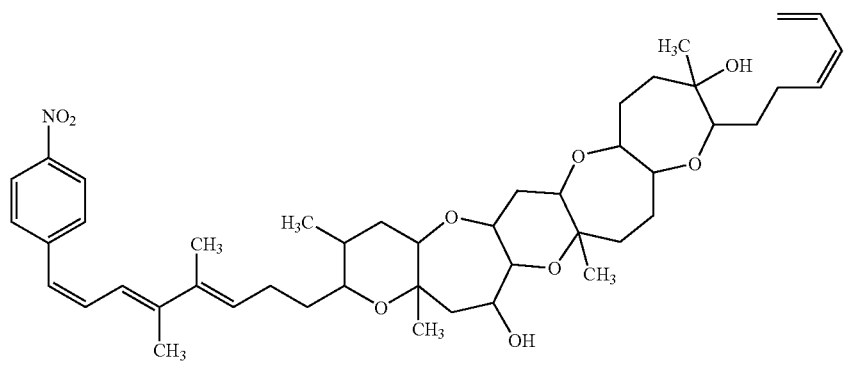
In another preferred embodiment, the compound of Formula (I) is:
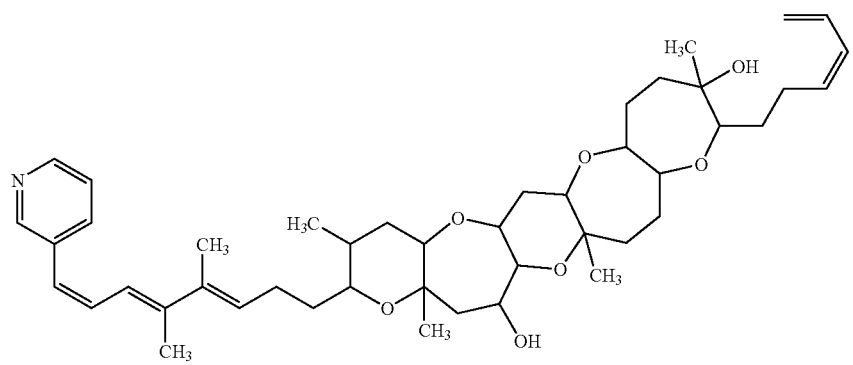

In another preferred embodiment, the compound of Formula (I) is:
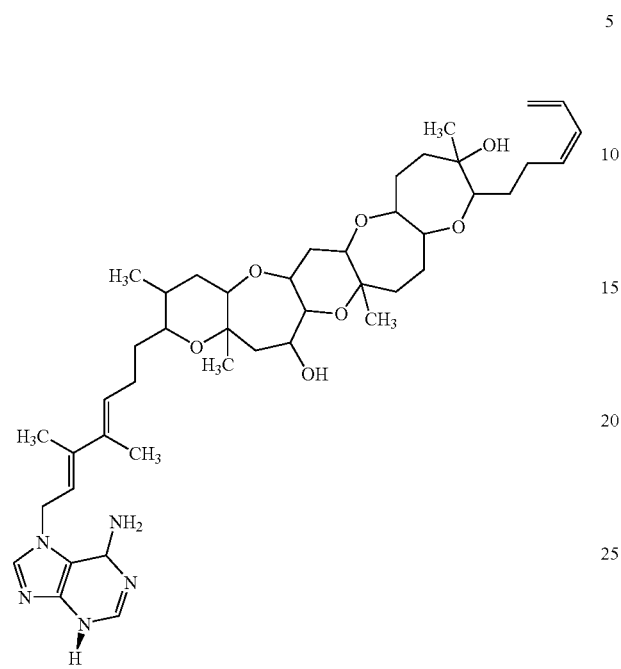
In another preferred embodiment, the compound of Formula (I) is:
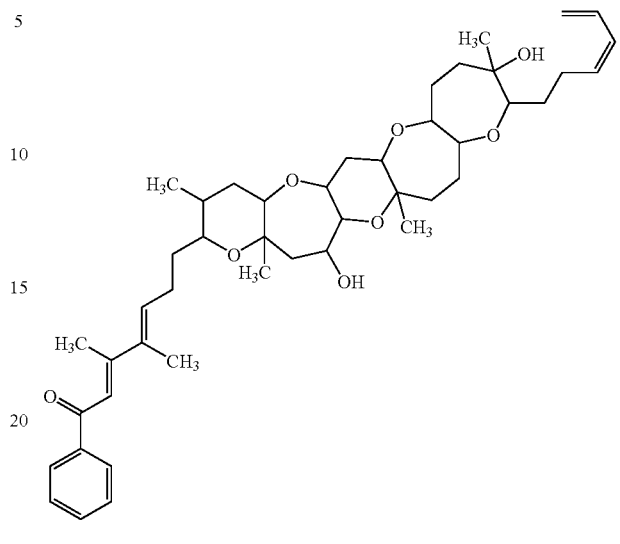
In another preferred embodiment, the compound of Formula (I) is:
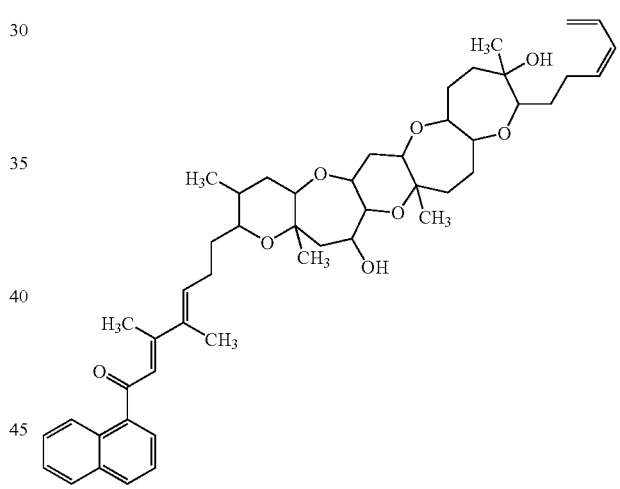
In another preferred embodiment, the compound of Formula (I) is:
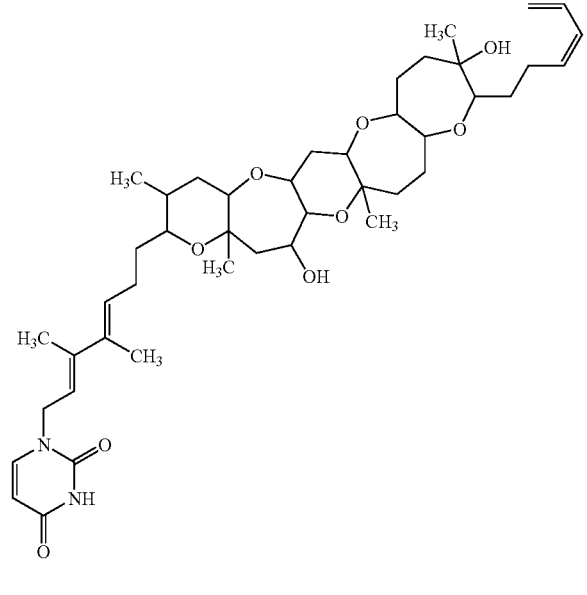
In another preferred embodiment, the compound of Formula (I) is:
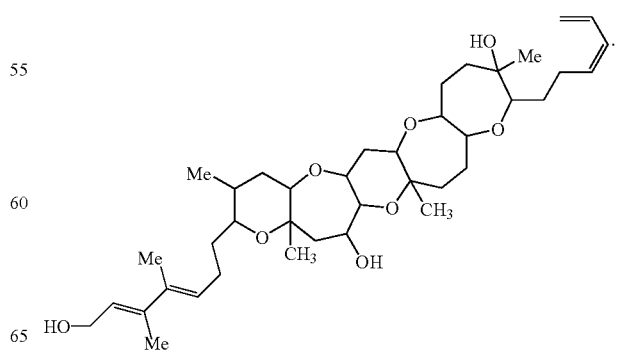

In one aspect of this preferred embodiment, the compound of Formula (I) is:
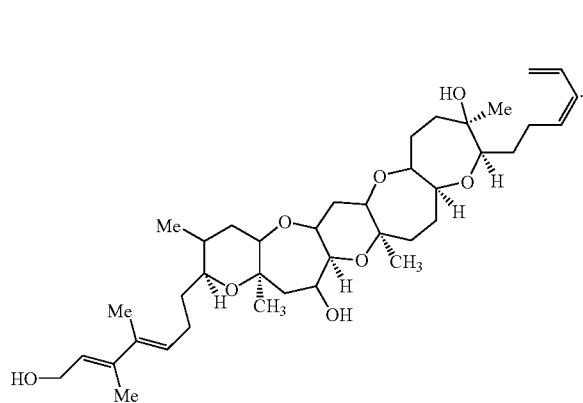
In another preferred embodiment, the compound of Formula (I) is:
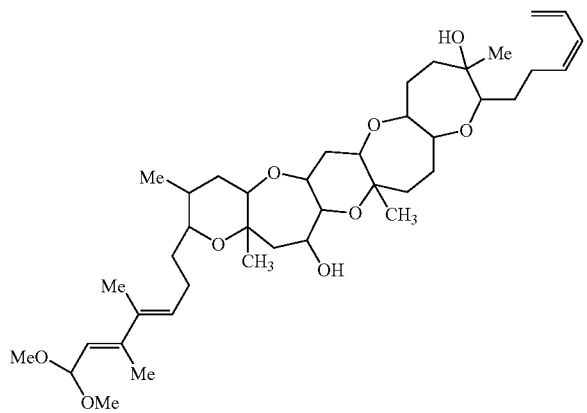
In one aspect of this preferred embodiment, the compound of Formula (I) is:
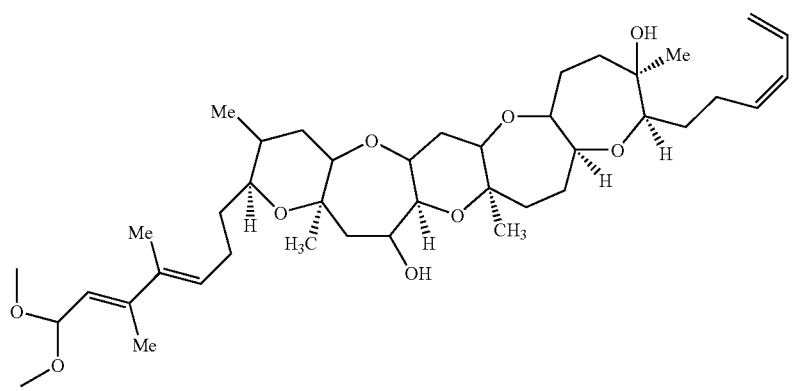
In another preferred embodiment, the compound of Formula (I) is:
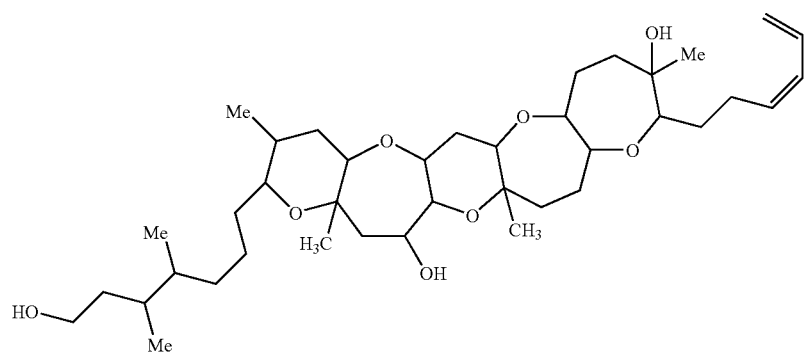

In one aspect of this preferred embodiment, the compound of Formula (I) is:

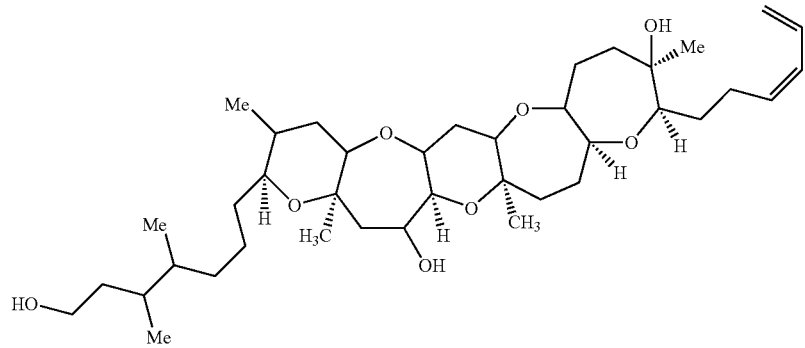

In another preferred embodiment, the compound of Formula (I) is:

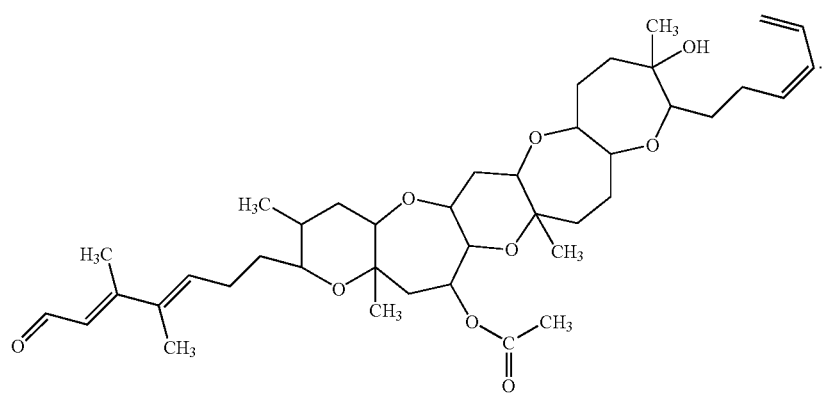

The compounds of Formula (I) may have asymmetric centers and occur as racemates, racemic mixtures and as individual diastereomers, or enantiomers. All isomeric forms are included within the scope of the present invention.

In a preferred aspect, the compounds of the invention are based on the brevenal core, i.e., each stereocenter in the compounds of formula (I) have the same configuration as the stereocenters in brevenal.

In another aspect, the invention relates to pharmaceutical compositions comprising a compound of formula I or a pharmaceutically acceptable salt, solvate, or hydrate thereof, and a pharmaceutically acceptable carrier, excipient, solvent, adjuvant or diluent.

In another aspect, the invention provides methods for regulating mucus clearance comprising administering to a subject, or contacting a cell with, a compound, salt, solvate or hydrate of the invention, or a pharmaceutical composition comprising a compound, salt, hydrate, or solvate of the invention, in an amount effective to regulate mucus clearance in the subject or cell.

As used herein decreases in mucus clearance or mucociliary dysfunction are generally measured by tracheal mucus transport (TMV), a surrogate marker for whole lung clearance.

In another aspect, the invention provides methods for treating conditions or diseases related to, or associated with, decreased mucus clearance comprising administering to a subject a compound of the invention, or pharmaceutical composition comprising a compound of the invention or a pharmaceutically acceptable salt, hydrate, ester, amide solvate, or mixtures thereof, in an amount effective to treat the condition or disease. This method of treating conditions or diseases associated with decreased mucus clearance can help prevent, treat, reduce the severity of, or delay the onset or progression of symptoms and disease states associated with decreased mucus clearance. Such conditions or diseases include the non-limiting examples of chronic obstructive airway disease (also known as chronic obstructive pulmonary disease (COPD)); asthma; cystic fibrosis, bronchoconstriction, and other pulmonary diseases; including pulmonary infections, such as the non-limiting examples pneumonia, *Pseudomonas*, and bronchitis; and cystic fibrosis.

In one embodiment, the method of treatment can be used to treat chronic obstructive pulmonary diseases, such as emphysema, pulmonary fibrosis, and/or smokers cough.

In one embodiment, the method of treatment can be used to treat asthma.

In one embodiment, the method of treatment can be used to treat pulmonary disease.

In one embodiment, the method of treatment can be used to treat pulmonary infection, including, but not limited to, pneumonia, or *Pseudomonas*.

In one embodiment the method of treatment can be used to treat poisoning by brevetoxins or ciguatoxin, and the symptoms thereof In a preferred embodiment, the method of treatment can be used to where the disease is cystic fibrosis.

In another aspect, the invention provides methods for treating the symptoms related to conditions or diseases associated with decrease mucus clearance or mucociliary dysfunction, comprising administering to a subject in need of such treatment, a therapeutically effective amount of a compound of the invention, or a pharmaceutically acceptable salt, hydrate, or solvate thereof.

In an embodiment of this aspect the methods of the invention can be used to treat diseases associated with mucus membranes, including such diseases involving pancreas, intestines, kidneys, fallopian tubes, and/or vas deferens.

In another embodiment of this aspect, the method can optionally comprise, in combination with a compound of Formula (I) or a pharmaceutically acceptable salt, solvate, or hydrate thereof, an effective amount of a compound known to be useful for the treatment of conditions or diseases associated with decreased mucus clearance. The methods of the invention can optionally comprise additional therapeutic regimen such as supportive or adjuvant therapy.

In one embodiment of the methods of the invention, the subject is an animal. More preferably, the animal is a mammal. Still more preferably, the mammal is a human.

In another embodiment, the animal is a companion animal, such as, for example, a horse, dog or cat.

The therapeutically effective amounts of the compounds of the invention suitable for the methods are generally from about 0.1 pg/day to about 1000 mg/day. The therapeutically effective amounts will vary according to various parameters including, for example, the particular therapeutic use and physical characteristics of the subject/patient, and are well within the knowledge of those skilled in the art.

In a preferred aspect, the therapeutically effective amount for oral administration is from about 1 mg/day to about 1000 mg/day. In another aspect, from about 1 mg/day to about 500 mg/day. In still another aspect, from about 1 mg/day to about 100 mg/day. In yet another aspect, from about 0.1 mg/day to about 10 mg/day.

In another aspect, the therapeutically effective amount is administered in a dosage of between about 1 mg to about 500 mg per dose.

In still another aspect, the therapeutically effective amount comprises a dosage of between about 1 mg to about 100 mg per dose.

Preferred dosages for administration by inhalation are from about 0.1 pg to about 1 µg per day.

Preferred dosages for administration by injection, i.e., parenteral administration, are from about 100 ng to about 1 mg per day.

The present invention also includes the use of a compound of Formula (I), or a pharmaceutically acceptable salt thereof for the manufacture of a medicament for use in treating a subject who has, or in preventing a subject from developing, NSP and/or CFP and symptoms associated with those poisonings, and who is in need of such treatment.

In one aspect, this use of a compound of formula (I) can be employed where the disease or condition is chronic obstructive pulmonary disease.

In another aspect, this use of a compound of formula (I) can be employed where the disease or condition is asthma.

In another aspect, this use of a compound of formula (I) can be employed where the disease or condition is pulmonary disease.

In another aspect, this use of a compound of formula (I) can be employed where the disease or condition is pulmonary infection.

In another aspect, this use of a compound of formula (I) can be employed where the disease or condition is cystic fibrosis.

In another aspect, this use of a compound of formula (I) can be employed where the disease or condition is chronic bronchitis.

In another aspect, this use of a compound of formula (I) can be employed where the disease or condition is Karteneger's syndrome.

In another aspect, this use of a compound of formula (I) can be employed where the disease or condition is bronchiectasis.

In another aspect, this use of a compound of formula (I) can be employed where the disease or condition is an industrial related disease caused or exacerbated by inhaling gases, particles of textiles, grit, or other industrial particles or fumes. Specific examples of particles and grit include, for example, iron oxides, silica, talc, carbon, graphite, fibers, wood dust, grain dust, organic solvents and pollutant gases.

In still another aspect, the compounds of formula (I) and the pharmaceutical compositions comprising formula (I) can be employed where the disease or condition results from inhalation of bacterial or other pathogenic particles, e.g., fungal particles. Thus, the invention also encompasses methods of clearing pathogenic particles, such as particles that comprise bacteria, e.g., anthrax or fungus particles.

The present invention also includes a container kit including a plurality of containers, each container including one or more unit dose of a compound of formula (I), or a pharmaceutically acceptable salt thereof.

In an embodiment, this container kit includes each container adapted for oral delivery and includes a tablet, gel, or capsule or inhaler.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The compounds of formula (I) can form salts when reacted with appropriate acids or bases. Pharmaceutically acceptable salts are generally preferred over the corresponding compounds of formula (I) since they frequently produce compounds that are usually more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include acid addition salts of both inorganic and organic acids. Preferred pharmaceutically acceptable salts include salts such as those described by Berge, Bighley, and Monkhouse, J. Pharm. Sci., 1977, 66, 1–19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. For other acceptable salts, see *Int. J. Pharm.*, 33, 201–217 (1986).

Hydrates and solvates of the compounds along with polymorphs thereof are also forms of the compounds of the invention and may be formed according to techniques known to one having ordinary skill in the pharmaceutical arts. The invention further includes complexes, particularly organo-metallic complexes, of the compounds of the invention. Complexes can be prepared when appropriate using processeses known in the art.

METHODS OF THE INVENTION

The compounds of the invention, pharmaceutical formulations comprising said compounds, and pharmaceutically acceptable salts thereof, are useful for treating a subject, preferably a mammal, more preferably a human, suffering from a disease or condition associated with decreased mucus clearance, and are useful for helping to prevent or delay the onset of such a disease or condition. The compounds and formulations of the invention are particularly useful for treating, preventing, or slowing the progression of chronic obstructive pulmonary disease, asthma, pulmonary disease, pulmonary infection, and cystic fibrosis. When treating or preventing a disease and condition associated with decreased mucus clearance, and the associated symptoms, the compounds of the invention can either be used individually or in combination, as is best for the subject.

With regard to these diseases and conditions, the term "treating" means that compounds of the invention can be used in subjects, preferably human subjects/patients, with existing condition or disease. The compounds of the invention will not necessarily cure the subject who has the disease but will delay or slow the progression or prevent further progression of the disease thereby giving the individual a more useful life span.

The term "preventing" means that that if the compounds of the invention are administered to those who do not now have the disease, or symptom(s) of the condition, but who would normally develop the disease or be at increased risk for the disease, they will not develop the disease. In addition, "preventing" also includes delaying the development of the disease in an individual who will ultimately develop the disease or would be at risk for the disease due to age, familial history, genetic or chromosomal abnormalities, and/or due to the presence of one or more biological markers for the disease. By delaying the onset of the disease, compounds of the invention can prevent the individual from getting the disease during the period in which the individual would normally have gotten the disease or reduce the rate of development of the disease or some of its effects but for the administration of compounds of the invention up to the time the individual ultimately gets the disease. Preventing also includes administration of the compounds of the invention to those individuals thought to have predisposition for the disease.

In a preferred aspect, the compounds of the invention are useful for slowing the progression of disease symptoms.

In another preferred aspect, the compounds of the invention are useful for preventing the further progression of disease symptoms.

In treating or preventing the above diseases, the compounds of the invention are administered in a therapeutically effective amount. The therapeutically effective amount will vary depending on the particular compound used, the physical characteristics of the subject to be treated, and the route of administration, as is known to those skilled in the art.

In treating a subject displaying any of the diagnosed above conditions a physician may administer a compound of the invention immediately and continue administration indefinitely, as needed.

Dosage Forms and Amounts

The compounds of the invention can be administered by inhalation, orally, parenterally, (IV, IM, depo-IM, SQ, and depo SQ), sublingually, intranasally, intrathecally, topically, vaginally, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

About 1 pg to about 100 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 0.1 pg to about 100 mg, preferably about 0.1 pg to about 10 mg, more preferably about 0.1 pg to about 10 pg, or about 1 pg to about 10 mg, of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare pharmaceutically acceptable compositions of the invention, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the subject treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of (administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on the route of administration, and the distribution, metabolism, and excretion rates of the compound, as well as the dosage schedule, and amount administered, together with other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed or blended with other pharmaceutically acceptable active agents that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered by inhalation (either orally or intranasally), orally, parenterally (IV, IM, depo-IM, SQ, and depo-SQ), sublingually, intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the subject 1, 2, 3, or 4, or more or as needed, times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

As noted above, depending on whether asymmetric carbon atoms are present, the compounds of the invention can be present as mixtures of isomers, as racemates, or in the form of pure isomers.

Salts of compounds are preferably the pharmaceutically acceptable or non-toxic salts of compounds of formula I. For isolation and purification purposes it is also possible to use pharmaceutically unacceptable salts.

EXAMPLES

Example 1

Synthesis of Compounds

Brevenal Isolation

Brevenal can be isolated and purified from native sources, such as *K. brevis*, or other red tide organisms. Suitable purification methodologies are well known in the art. See, for example, Baden et al, 1981, *Toxicon* 19:455–463; Poli et al., *Molecular Pharmacology*, 1986 30:129–135. The following procedure is representative.

Brevenal is extracted from *K. brevis* cultures (Provasoli—Guillard National Center for Culture of Marine Phytoplankton, West Boothbay Harbor, Me.) using chloroform. The chloroform layers are collected, dried and partitioned between petroleum ether and aqueous methanol to remove pigments and cellular lipid debris. The aqueous methanol layer (90%) is dried under vacuum and the components separated using a silica gel column (mobile phase $CHCl_3$:methanol:acetic acid; 100:10:1 v/v). Brevenal and brevetoxins coelute from the silica column; fractions containing these materials are collected and combined. A low-pressure C18 matrix column is used to separate the remaining pigments from brevetoxins and brevenal using an acetonitrile:water mobile phase (80:20 v/v), creating a "clarified" extract. The clarified extract is applied to an HPLC column, such as a Varian C18 reverse-phase column (0.8×25 cm) with a running buffer of 90:10 methanol:water at an appropriate pump rate (e.g., 3–4 mL/min). Detection of eluate peaks can be done by any method known in the art, such as UV detection at 215 nm. Peaks of interest are isolated and applied to another column, such as a hydrophobic interaction (HI) column (e.g., Phenomenex C18 phenyl-hexyl column 0.8× 25 cm) in appropriate running buffer (e.g., 99% MeOH:1% H2O). The fractions containing the compound(s) of interest are pooled and the compound(s) are isolated by any known method such as crystallization, evaporation of solvent (Roto-Vap).

The structure of brevenal was determined using a number of spectroscopic methods including NMR, Mass spectroscopy and FT-IR. The exact mass of brevenal as determined by high resolution Mass Spectroscopy is 656.4043. The primary and stereospecific structure were elucidated using 1-D and 2-D NMR spectroscopy in four different solvents.

Various synthetic methodologies can be used to make compounds of the invention; brevenal is a suitable starting material. Suitable methodologies are known in the art. Brevenal can be used as a starting material as is or can first be protected or converted to the corresponding alcohol or carboxylic acid for subsequent elaboration. Representative synthetic procedures for preparing compounds of the invention from such starting materials are disclosed in, e.g., Mende, T. J., et al., *Tetr. Lett.*, 1990; 31(37):5307–5310; Trainer, V. L., et al., *Molec. Pharm.*, 1991; 40(6):988–994; Keck, G. E., et al., *Tetrahedron Lett.*, 1987, 28:139–142; Alvarez, E., et al., *Chem. Rev.*, 1995, 95:1953–1980; Rein, et al., 1994: (a) *J. Org Chem.*, 59:2107–2113; (b) *J. Org. Chem.* 59:2101–2106. Each of these references is incorporated herein by reference in its entirety. Those skilled in the art will appreciate that minor modifications can be made to the particular procedures to arrive at compounds of the invention.

Example 1

α-Amiloride Derivative

Amiloride (N-amidino-3,5-diamino-6-chloropyrazinecarboxamide) exists in charged form under physiological conditions as shown below.

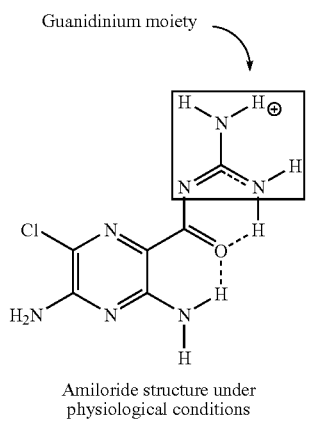

Amiloride structure under physiological conditions

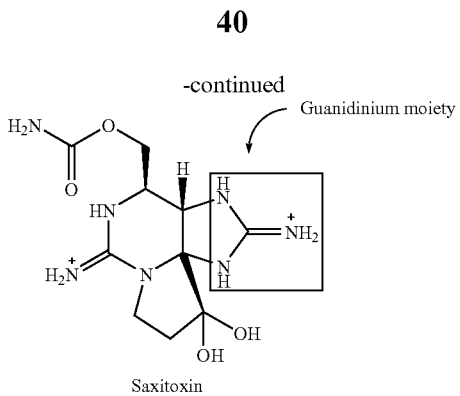

-continued

Saxitoxin

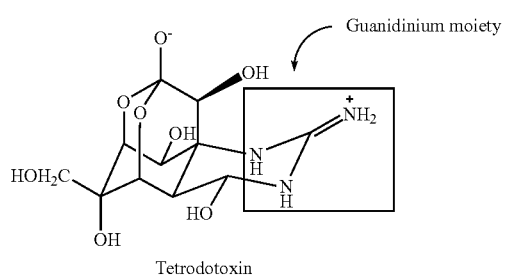

Tetrodotoxin

Amiloride, Saxitoxin and Tetrodotoxin Structures

Amiloride Functionalization of Brevenal:

Introduction of a guanidine moiety on the brevenal sidechain is performed as follows. Brevenal is treated with sodium chlorite and sodium dihydrogenphosphate in a solvent mixture of tert-butanol/2-methyl-2-butene to lead to the acid brevenal derivative 2 (scheme 2). Treatment of 2 with CDI in DMF followed by addition of guanidine (free base) or guanidine carbonate affords the guanidine compound 3.

Scheme 2: Guanidine introduction on the α, β unsaturated aldehyde sidechain of brevenal Brevenal

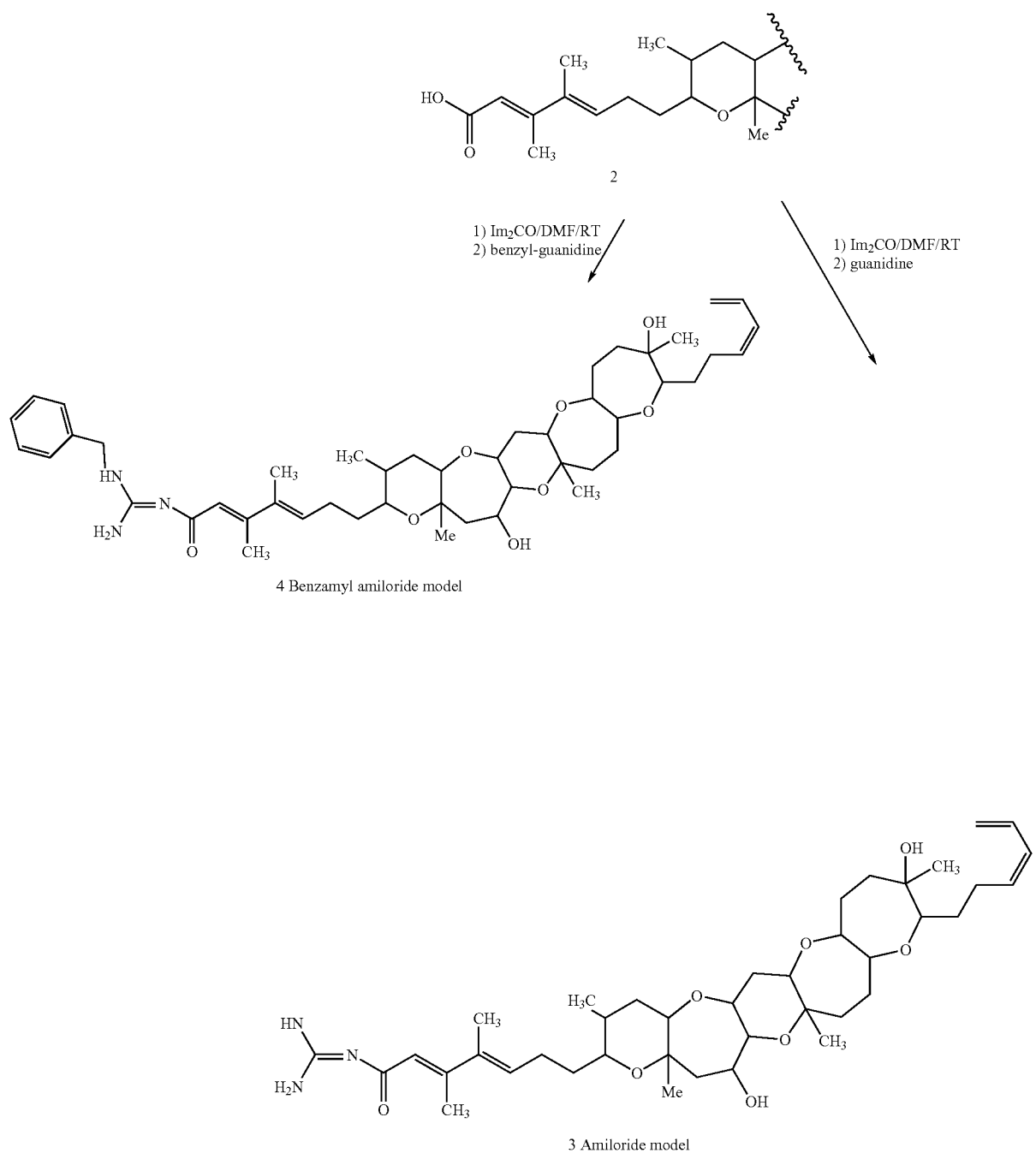
Preparation of Benzamyl Guanidine Brevenal:
The synthesis is performed by essentially following the same procedure as described for the synthesis of 3 with addition of benzamyl guanidine instead of guanidine (scheme 2). Alternatively, Brevenal can be converted into the corresponding acid chloride to effectuate the conversion to the guanidine derivatives.

Example 2

β-Naphthoyl Derivative

β-naphthoyl brevenal is prepared as follows. A solution of carbonyldiimidazole and 2-naphthoic acid in benzene is added to brevenol and refluxed overnight to furnish β-naphthoyl brevenal 5 (scheme 3).

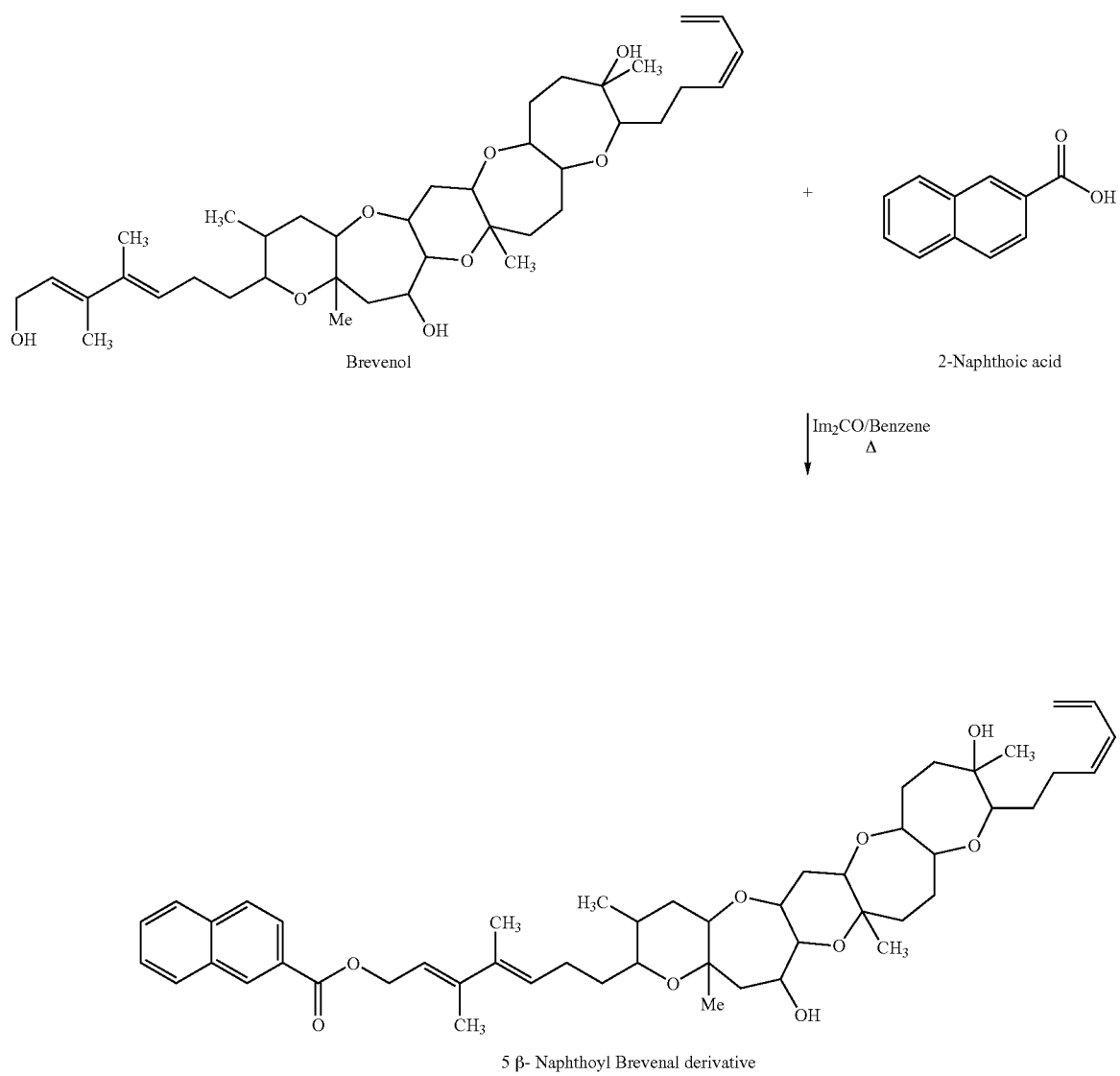

Brevenal is treated with sodium borohydride and cerium chloride in a mixture of DMF/methanol. After an ether extraction, the crude extract is purified on HPLC to give brevenol with good yield. Alternatively, Brevenal can first be converted into the corresponding carboxylic acid and reacted subsequently reacted with an appropriate alcohol to afford an ester.

Example 3
Aromatic Brevenal
A. Introduction of the hydroxy benzyl moiety is achieved through a Grignard reaction between phenylmagnesium bromide and brevenal (scheme 4). Extraction followed by purification affords an ephedrine adduct of brevenal 6.
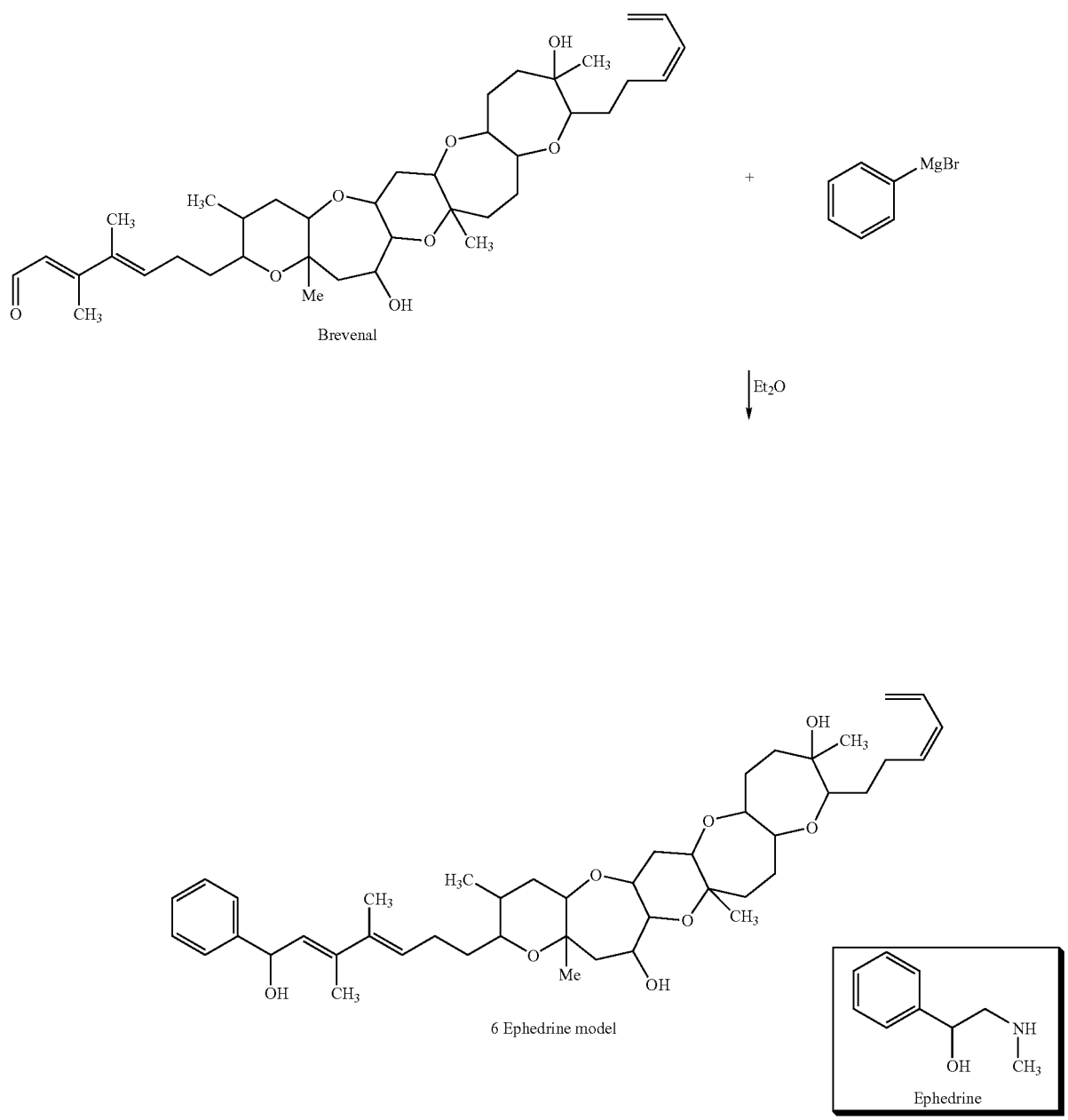

B. A one step synthesis can be used to prepare several benzenic compounds. Using a Wittig reaction and commercially available phosphoranes, various derivatives involving a phenyl group can be made. Thus, treatment of phosphoranes 7a–7f with base followed by addition of brevenal furnishes the corresponding ethylenic compounds 8a–bf (scheme 5). Compounds may be further purified by HPLC.

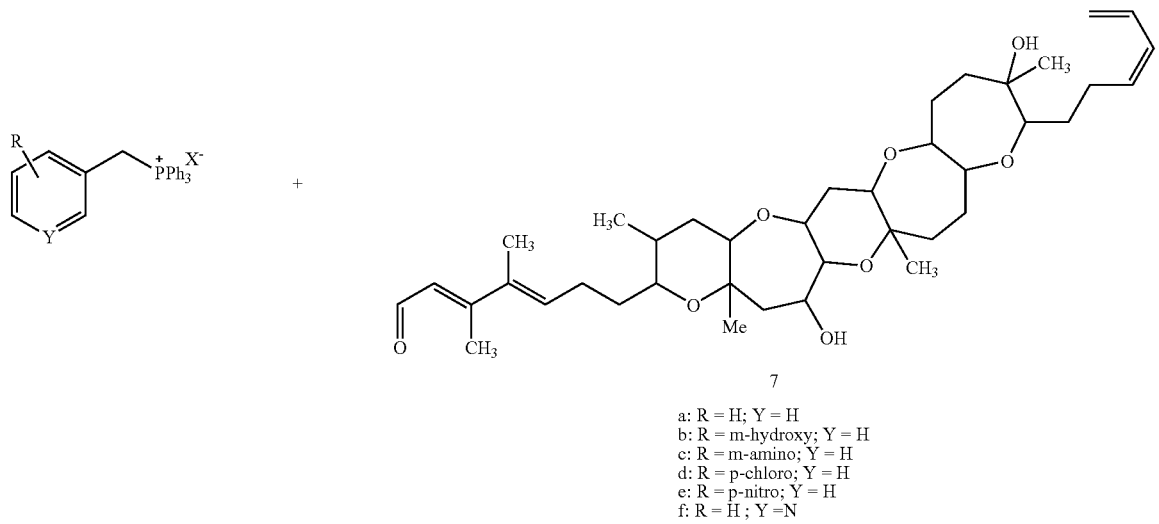

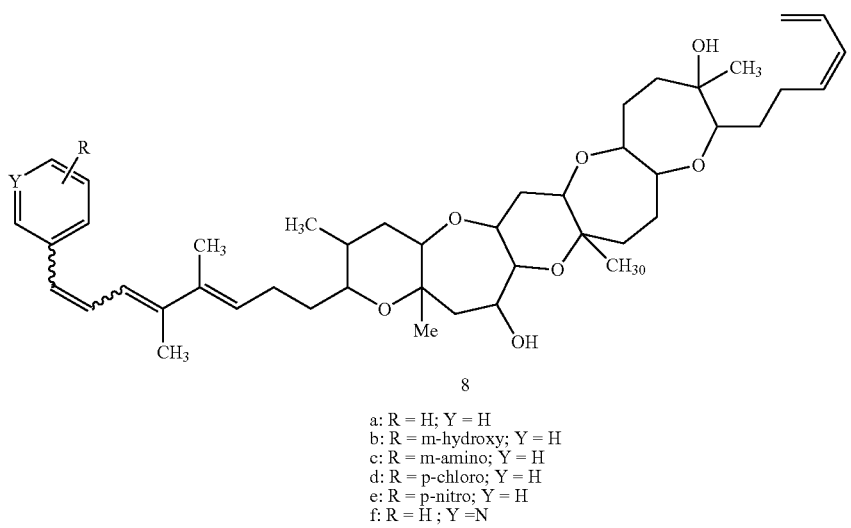

Example 4

Benzimidazolone Derivatives

The synthesis begins by the activation of brevenol into a mesylate intermediate followed by the deplacement of the mesylate by iodide to yield to iodo-brevenal derivative 9 (scheme 6). Then treatment of the commercially available 1,3-dihydro-benzimidazl-2-one with sodium hydride in DMF followed by addition of iodo-brevenal 9 furnishes, after extraction and purification, the benzimidazolone-brevenal derivative 10.

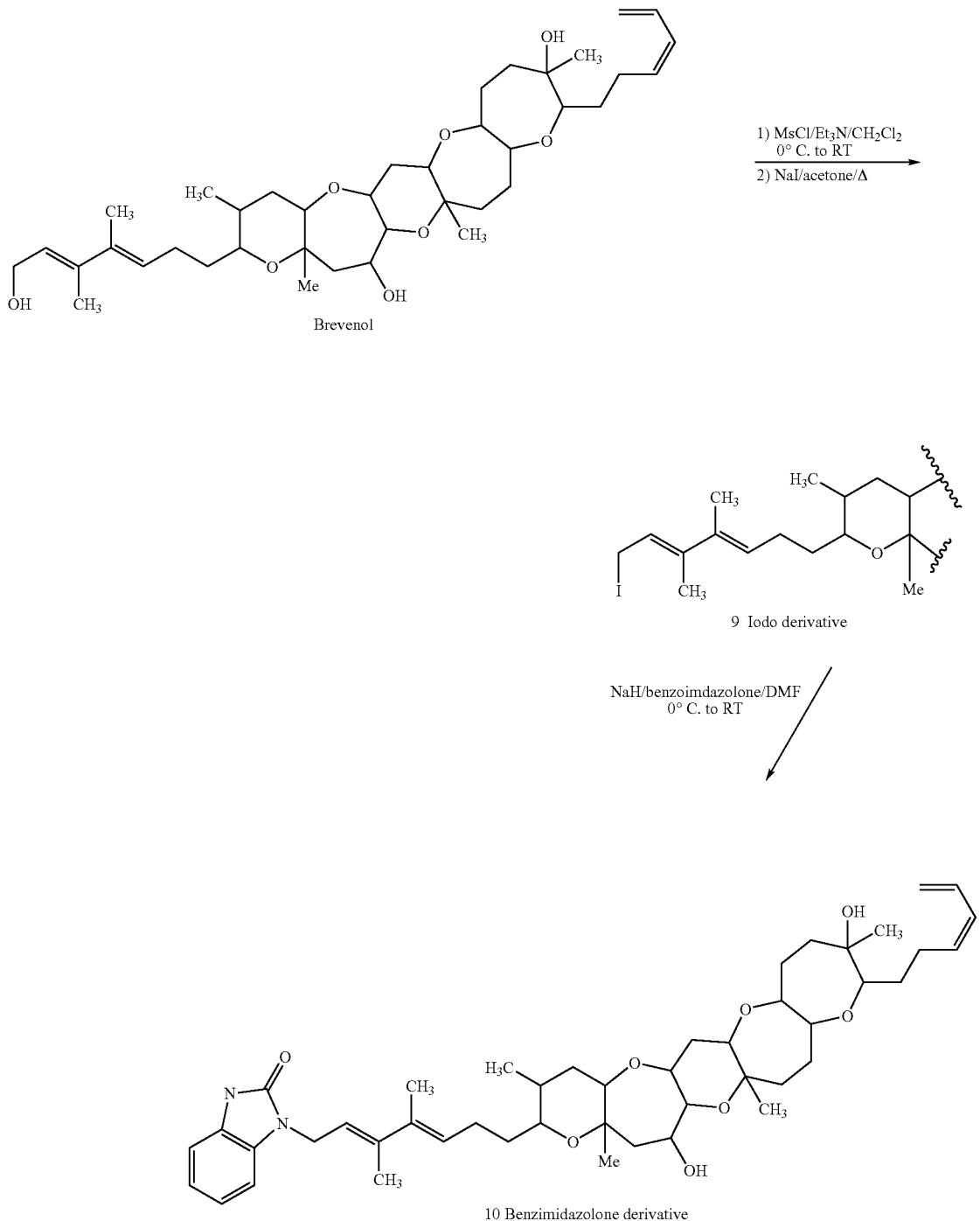

Scheme 6: Synthesis of a benzimidazolone model of brevenal

Example 5

Nucleoside Model of Brevenal

ATP or UTP is treated with dicyclohexylcarbodiimide in DMF to generate the reactive moiety that is then added to brevenol. The reaction mixture is heated under reflux and extracted. Purification of the crude extract affords the nucleotide derivatives 11 and 12 (scheme 7).

cm $H_2O$. Once the balloon is placed, it is secured so that it remains in position for the duration of the experiment. Lateral pressure in the trachea is measured with a sidehole catheter (inner dimension, 2.5 mm) advanced through and positioned distal to the tip of the endotracheal tube. Transpulmonary pressure, the difference between tracheal and pleural pressure, is measured with a differential pressure transducer catheter system which shows no phase shift between pressure and flow up to a frequency of 9 Hz. For the measurement of pulmonary resistance ($R_L$), the proximal end of the endotracheal tube is connected to a pneumotachograph (Fleisch, Dyna Sciences, Blue Bell, Pa.). The signals of flow and transpulmonary pressure are recorded on an oscilloscope recorder which is linked to a computer for on-line calculation of $R_L$ from transpulmonary pressure, respiratory volume (obtained by digital integration) and flow by the iso-volume technique. Analysis of 5–10 breaths is used for the determination of $R_L$ (Abraham et al., 1994).

Scheme 7: Synthesis of UTP- and ATP-Brevenal

Example 6

Airway Mechanics Experimental Protocols

Measurement of Airway Mechanics—Unsedated sheep are restrained in a cart in the prone position with their heads immobilized. After topical anesthesia of the nasal passages with 2% lidocaine solution, a balloon catheter is advanced through one nostril into the lower esophagus. The animals are intubated with a cuffed endotracheal tube through the other nostril using a flexible fiber optic bronchoscope. Pleural pressure is estimated with the esophageal balloon catheter (filled with one ml of air) which is positioned 5–10 cm from the gastroesophageal junction. In this position the end expiratory pleural pressure ranges between −2 and −5

Aerosol Delivery Systems—All aerosols are generated using a disposable medical nebulizer (Raindrop®, Puritan Bennett, Lenexa, Kans.) that provide an aerosol with a mass median aerodynamic diameter of 3.2 μm (geometric SD 1.9)

as determined by an Andersen cascade impactor. The nebulizer is connected to a dosimeter system, consisting of a solenoid valve and a source of compressed air (20 psi). The output of the nebulizer was directed into a plastic T-piece, one end of which is connected to the inspiratory port of a Harvard respirator. The solenoid valve is activated for one second at the beginning of the inspiratory cycle of the respirator. Aerosols were delivered at a tidal volume of 500 ml and a rate of 20 breaths per minute (Abraham et al., 1994).

Airway Responsiveness—To assess airway responsiveness, we perform cumulative dose response curves to carbachol by measuring $R_L$ immediately after inhalation of buffer and after each consecutive administration of 10 breaths of increasing concentrations of carbachol (0.25, 0.5, 1.0, 2.0 and 4.0% w/v buffered saline). The provocation test is discontinued when $R_L$ increased over 400% from the post-saline value or after the highest carbachol concentration has been administered. Airway responsiveness is estimated by determining the cumulative carbachol dose in breath units (BU) that increases $R_L$ by 400% (PC400) by interpolation from the dose response curve. One breath unit (BU) is defined as 1 breath of an aerosol solution containing 1% wt/vol carbachol (Abraham et al., 1994).

Nasal Airway Resistance—Nasal airway resistance (NAR) is measured with a modified mask rhinomanometry technique. The sheep's head is placed in a plexiglass hood with attachments for a faceplate containing a pneumotachograph to measure flow and two catheter ports to measure the pressure differential between nose and mouth pressure (Abraham et al., 1998).

Tracheal Mucus Velocity—Sheep are nasally intubated with an endotracheal tube 7.5 cm in diameter shortened by 6 cm., after topical anesthesia of the nasal passages with 2% lidocaine solution. The cuff of the tube is placed just below the vocal cords (verified by fluoroscopy) in order to allow for maximal exposure of the tracheal surface area. TMV is measured in vivo by a roentgenographic technique. Between 10 and 20 radiopaque Teflon/bismuth trioxide disks, 1-mm diameter, 0.8-mm thick and 1.8 mg in weight, are insufflated into the trachea via the endotracheal tube. The cephalad-axial velocities of the individual disks are recorded on videotape from a portable image intensifier unit. Individual disk velocities are calculated by measuring the distance traveled by each disk during a 1-min observation period. For each run, the mean value of all individual disk velocities is calculated. A collar containing radiopaque reference markers of known length are worn by the sheep, and used as a standard to correct for magnification effects inherent in the fluoroscopy unit (O'Riordan et al., 1997).

Statistical Analysis—If the data are normally distributed, then parametric statistics are used; if data do not conform to a normal distribution, non-parametric statistics are used. The basic statistical tests include analysis of variance (ANOVA), i.e. one-way ANOVA or two-way ANOVA with repeated measures for multipoint analysis, and unpaired or paired t-test for the appropriate single point analysis. The non-parametric counterparts of these tests are: a) the Mann-Whitney test, which is the counterpart of the unpaired t-test; b) Wilcoxon's signed ranks test, the counterpart of the paired t-test; c) Friedman's Analysis of Variance for related samples, i.e. randomized blocked design; d) the Quade test, also a randomized block design test but for use with small blocks (n≦4); e) the Kruskal-Wallis test, ANOVA for un-related samples; and f) a non-parametric pairwise comparison, analogous to the parametric Newman-Kuels pairwise test. Where applicable, linear regression analysis is performed by method of least squares, and correlations will be tested for with Spearman's rho test. For all studies, significance is accepted with p<0.05 on a two tailed analysis (Conover, 1980).

Example 7

Fish Bioassay

Male mosquito fish (n=104) were used in this assay. Fish were placed individually in 50 mL beakers containing 20 mL water. The test compounds (PbTx-2 and brevenal) were dissolved in EtOH at a concentration of 0.1 mg/mL and added to the fish in a total of 200 μL EtOH. The control fish received 200 uL EtOH. Fish were exposed to toxin alone (1 μg/mL water), brevenal alone (1 or 2 μg/mL water), or both brevenal (1.0 μg/mL water and toxin (1.0 μg/mL water) with the brevenal being added 3 min. before the toxin. After addition of the differenc compounds the fish were monitored for 24 h. or until the time of death. Significant differences were determined using a two-way Student's t-test.

Fish exposed to PbTx-2 only died within about 7.5 min., while fish exposed to control, or brevenal at 1 or 2 μg/mL did not die after 24 h. Brevenal effectively protected fish from an equal concentration of PbTx-2, prolonging life by ~2.5-fold (with fish dying at about 17 min. after exposure). This suggests that brevenal is not toxic at concentrations effective for brevetoxin antagonist activity.

Example 8

Competitive rat brain synaptosome assays were performed as described in Poli et al., 1986. The data show that tritiated brevetoxin PbTx-2 was effectively displaced (~80%) by brevenal and di-O-Me brevenal when the compounds were added at about 1000× the concentration of the tritiated PbTx-2. The approximate $EC_{50}$ for each are: 3.53 nM ($K_i$=1.76 nM) for PbTx-2; 3.69 uM ($K_i$=1.86 μM) for brevenal; 1.35 μM ($K_i$=0.68 μM) for di-O-Me brevenal.

The invention has been described with reference to various specific and preferred embodiments and techniques. However, it should be understood that many variations and modifications may be made while remaining within the spirit and scope of the invention.

What is claimed is:

1. A compound of the Formula:

wherein

R is $C_1$–$C_{12}$ alkyl, $C_2$–$C_{12}$ alkenyl, $C_1$–$C_{12}$ alkyl esters, $C_1$–$C_{12}$ alkyl amides, $C_4$–$C_{12}$ alkenyl esters, $C_1$–$C_{12}$ alkylaryl esters, $C_4$–$C_{12}$ alkenylaryl esters, $C_4$–$C_{12}$ alkenyl amides, $C_1$–$C_{12}$ alkoxy, formyl$C_1$–$C_{12}$alkyl, formyl$C_2$–$C_{12}$alkenyl, alkanoyl$C_1$–$C_{12}$alkyl, alkanoyl$C_2$–$C_{12}$alkenyl, carboxy$C_1$–$C_{12}$alkyl, or carboxy$C_2$–$C_{12}$alkenyl, wherein the alkyl and alkenyl groups are optionally substituted with 1–6 substituent groups selected from the group consisting of:

$C_3$–$C_{12}$ cycloalkyl, $C_3$–$C_{12}$ heterocyclyl, aryl, heteroaryl, $C_1$–$C_6$ alkyl, $C_1$–$C_6$ alkoxy, halogen, $C_2$–$C_6$ alkenyl, OH, aryl esters, cycloalkyl esters, cycloalkenyl esters, and

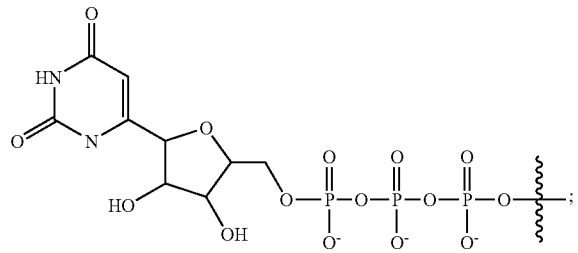

$OR_1$ is OH or —O(CO)$CH_3$;

$R_2$ is —CH═CHCH═$CH_2$, —$CH_2$-phenyl, or —$CH_2$-pyridyl, wherein the phenyl and pyridyl groups are optionally substituted at each substitutable position with a group that is independently $C_1$–$C_6$ alkyl, $C_1$–$C_6$ alkoxy, haloalkyl, haloalkoxy, hydroxy, hydroxyalkyl, halogen, —$CO_2$H, $C_1$–$C_6$ alkoxycarbonyl, —C(O)$NH_2$, —C(O)NH($C_1$–$C_6$ alkyl), or —C(O)N($C_1$–$C_6$ alkyl)($C_1$–$C_6$ alkyl); or pharmaceutically acceptable salts, solvates, esters, amides, or combinations thereof.

2. The compound according to claim 1, wherein R is

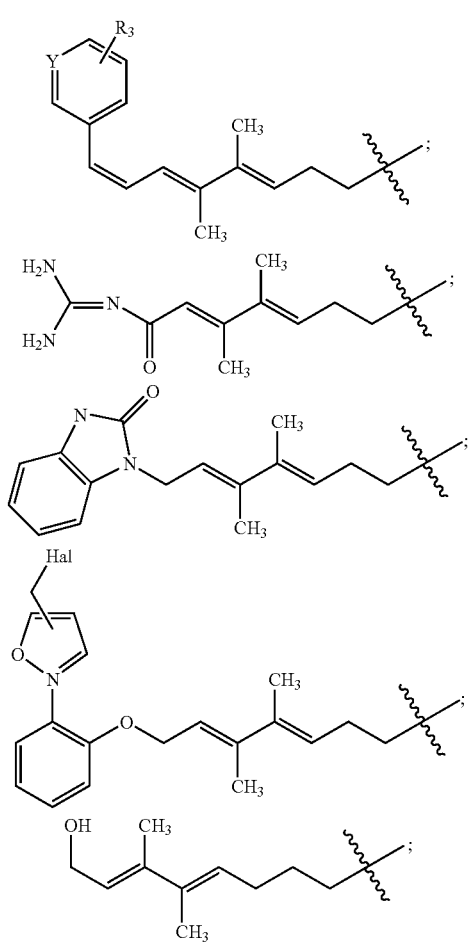

-continued

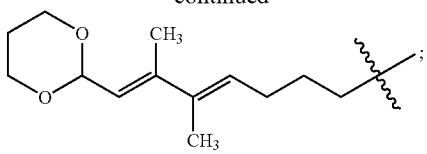

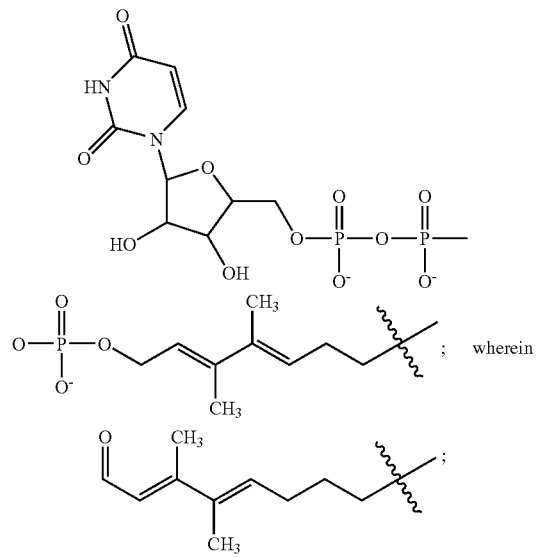; wherein

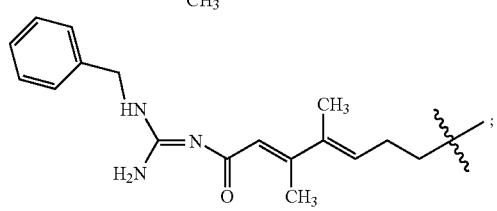

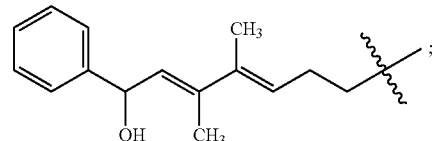

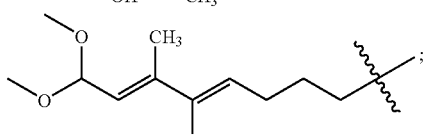

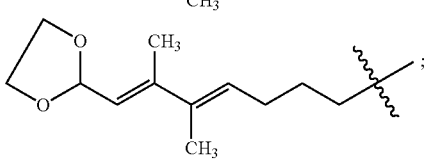

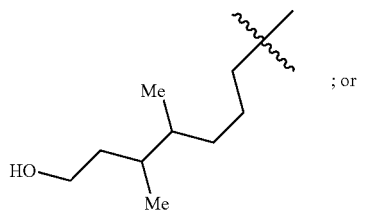

wherein

Hal is chloro, fluoro, iodo, or bromo;

$R_3$ is selected from H, OH, $NH_2$, halogen, and $NO_2$, and Y is selected from CH, N, O, and S.

3. The compound according to claim 1, wherein the compound is selected from the group consisting of:
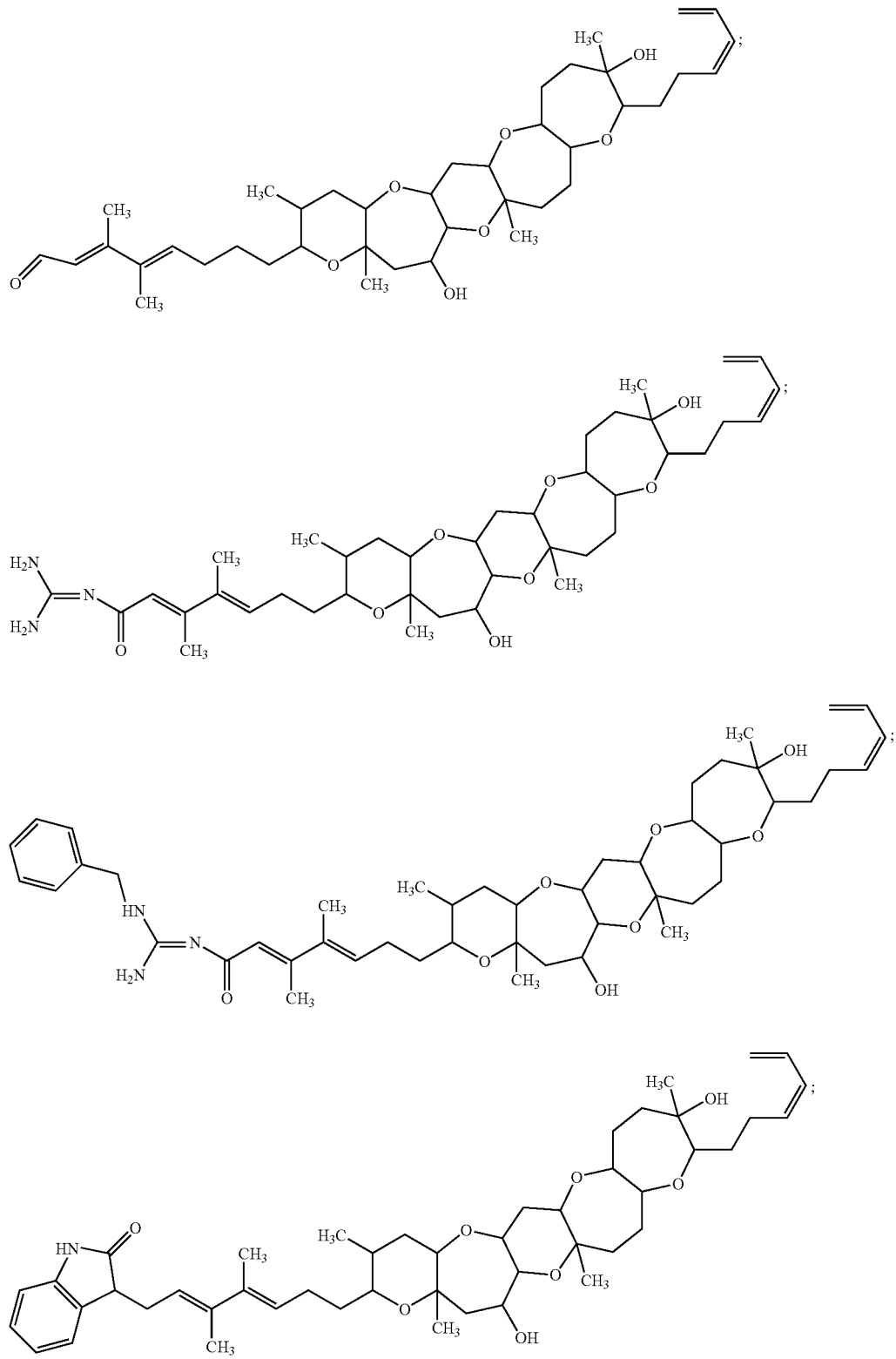

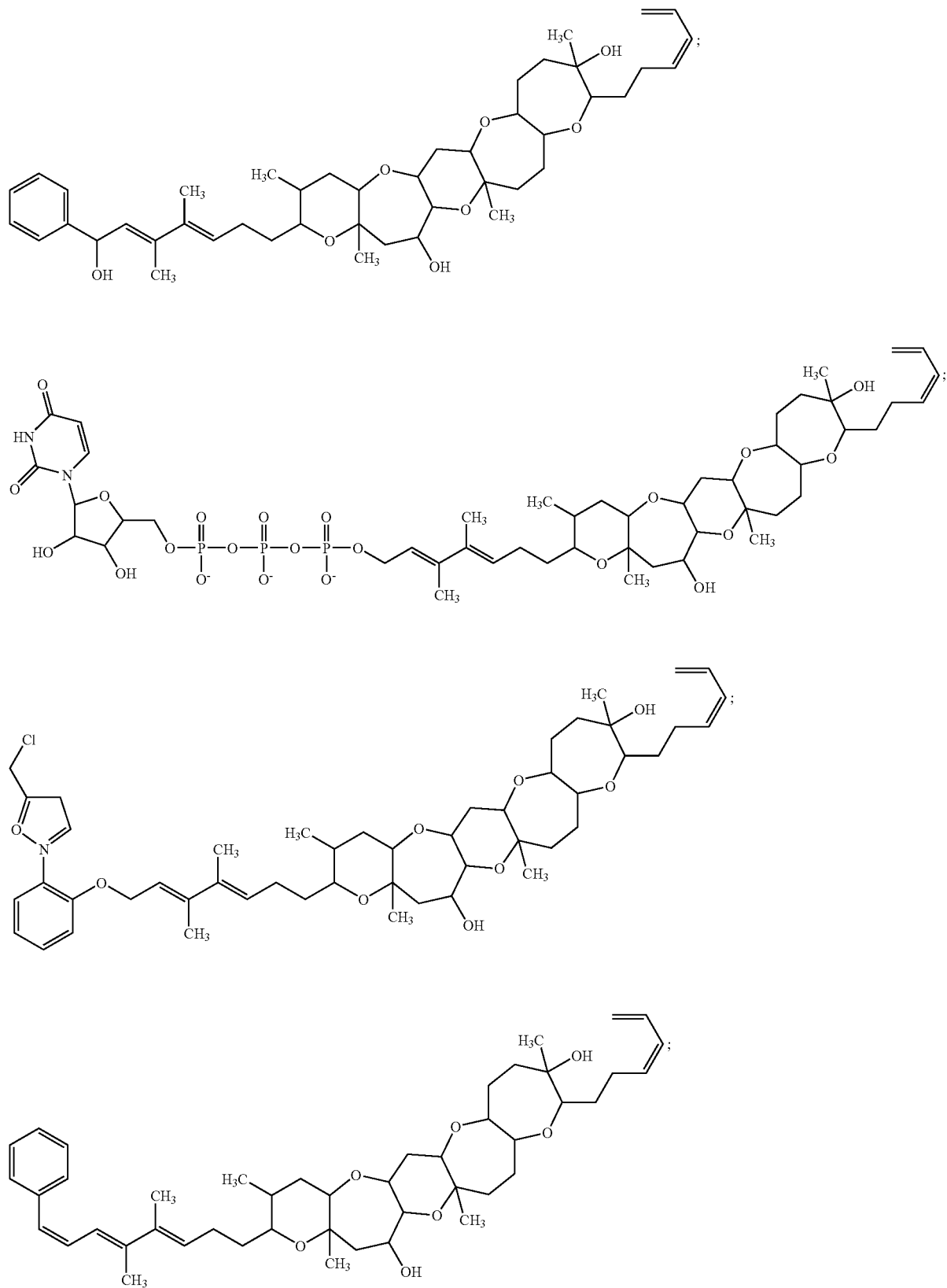

-continued
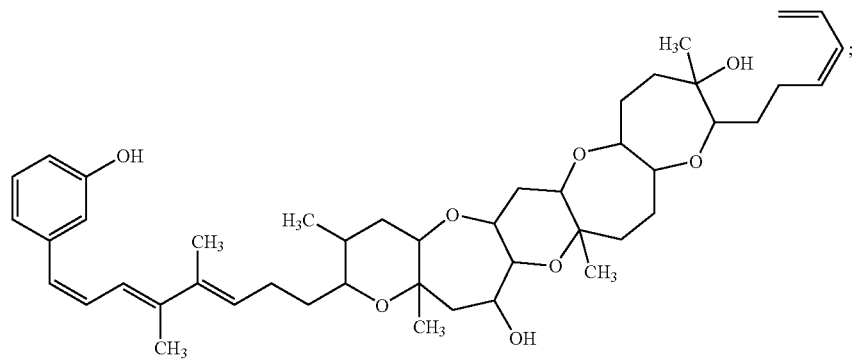
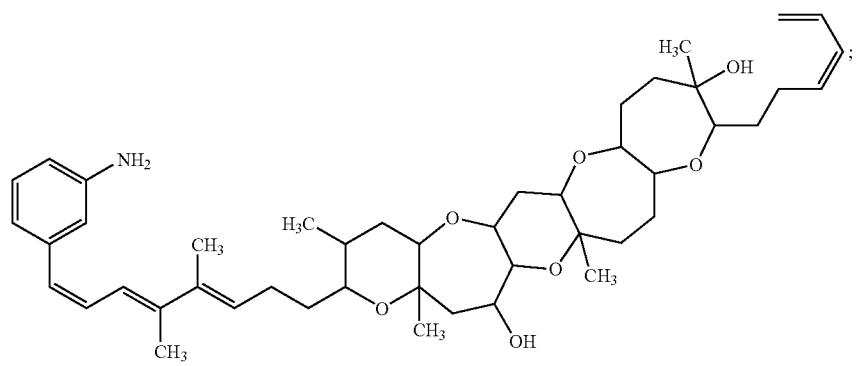
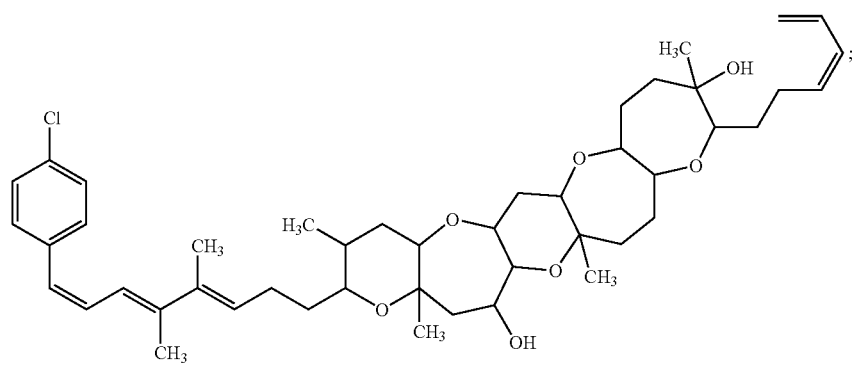
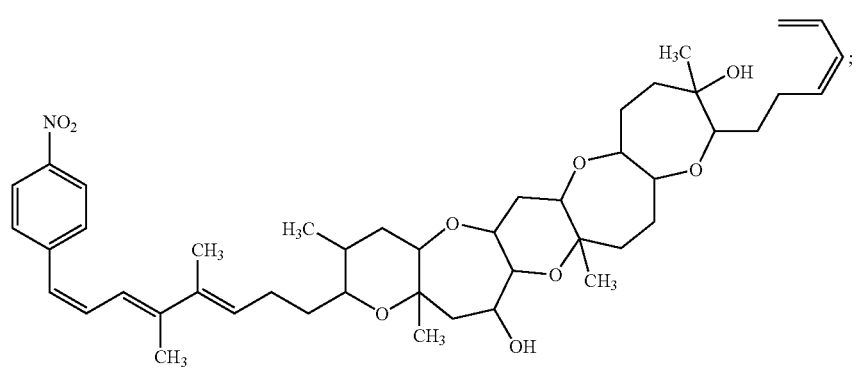

-continued
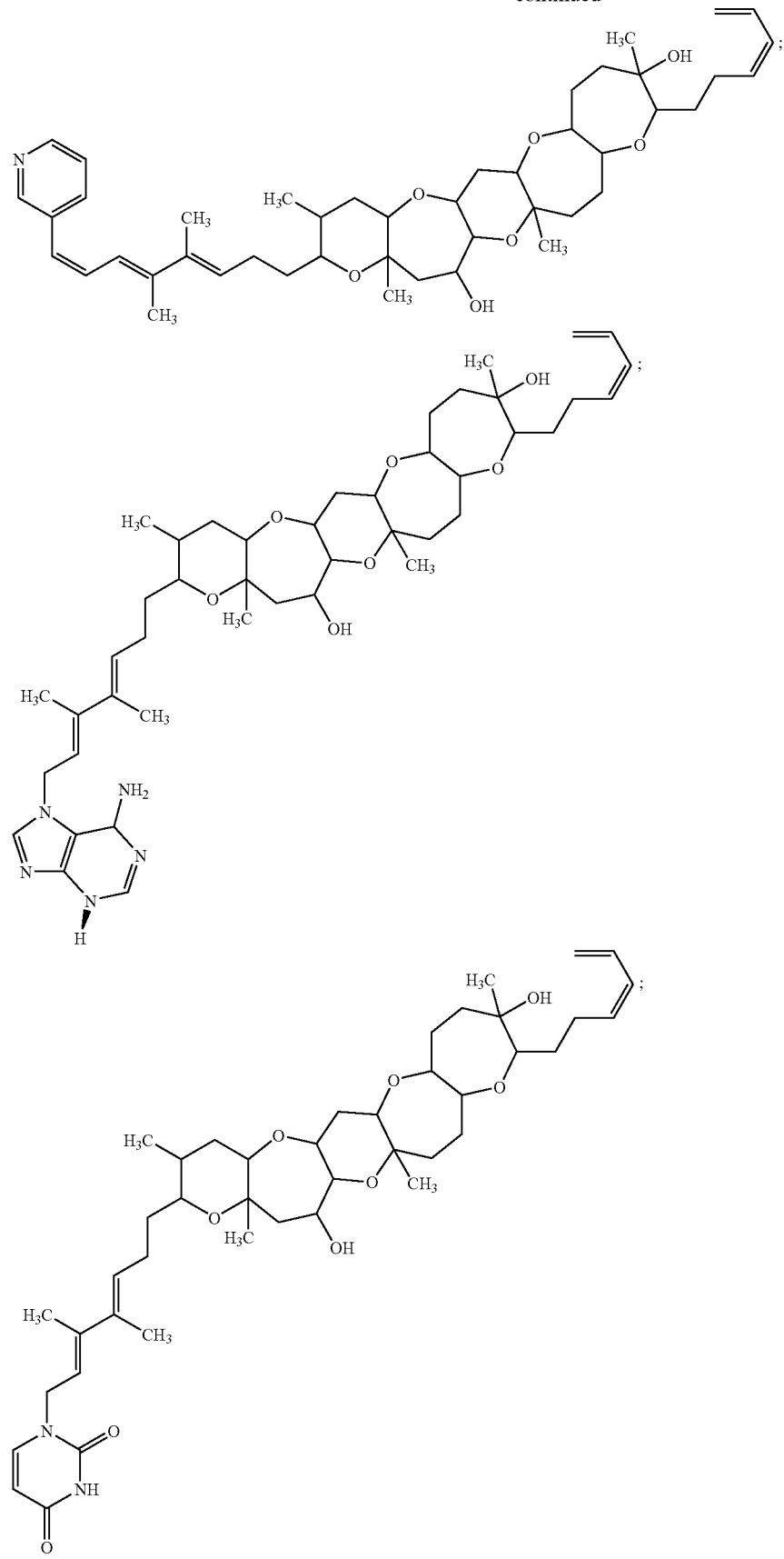

-continued
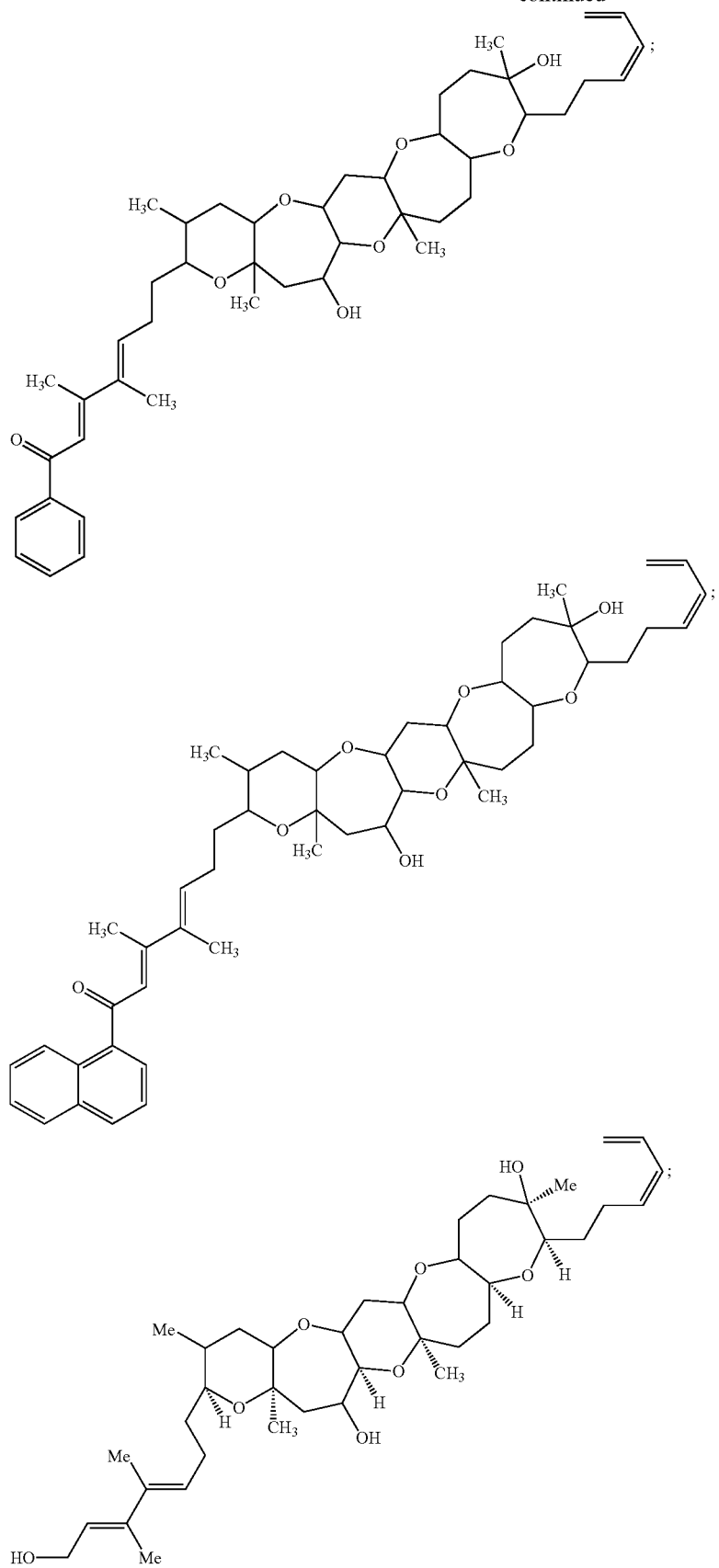

-continued

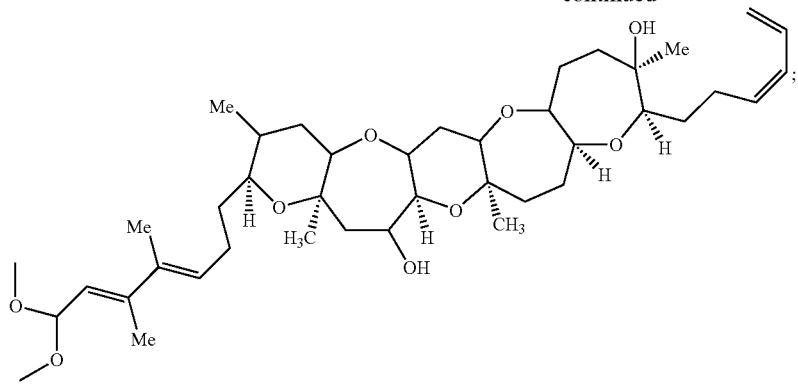

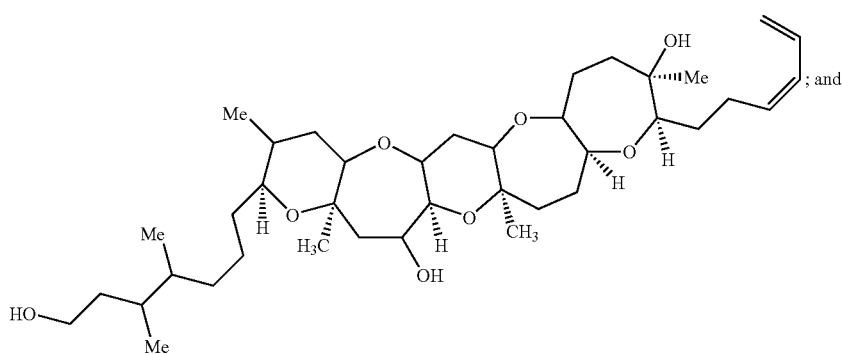

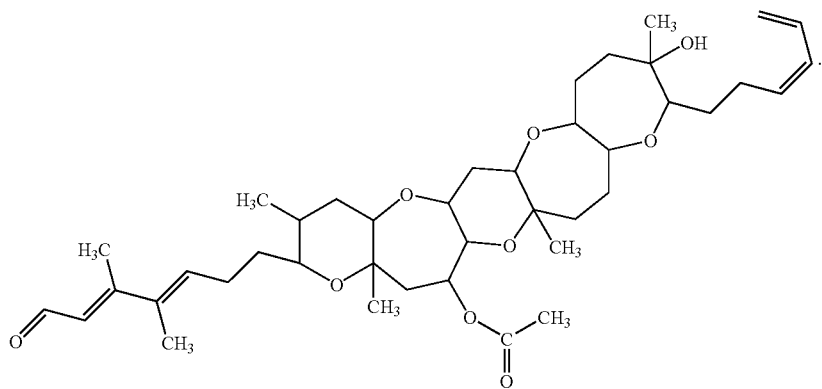

4. A pharmaceutical composition comprising a therapeutically effective amount of at least one compound, pharmaceutically acceptable salt, solvate, ester, amide, or isomer of claim 1, and at least one pharmaceutically acceptable carrier, excipient, solvent, adjuvant, diluent, or mixtures thereof.

5. A pharmaceutical composition of claim 4, wherein the pharmaceutical composition is in unit dosage form.

6. The pharmaceutical composition in unit dosage form according to claim 5, wherein the compound is present in an amount of about 1 pg to about 100 mg.

7. A compound of claim 1, wherein
R is
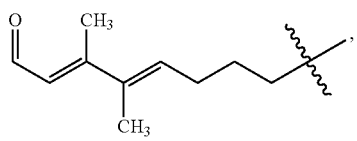
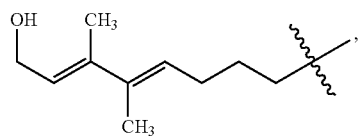
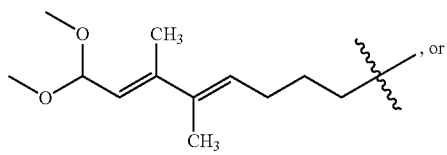, or
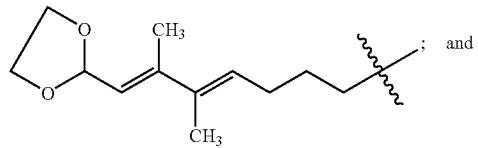; and
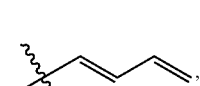
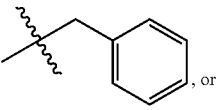, or
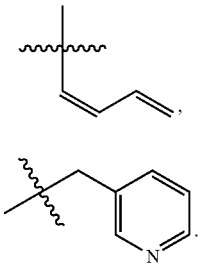.
8. A compound according to claim 7, wherein $R_1$ is H.
9. A compound according to claim 2, wherein $R_2$ is —CH=CHCH=CH$_2$.
* * * * *

UNITED STATES PATENT AND TRADEMARK OFFICE
CERTIFICATE OF CORRECTION

PATENT NO.       : 7,202,271 B2  
APPLICATION NO.  : 10/945471  
DATED            : April 10, 2007  
INVENTOR(S)      : Daniel G. Baden It is certified that error appears in the above-identified patent and that said Letters Patent is hereby corrected as shown below:

On the Title Page

Section   [75],   insert: Sophie Michelliza

Signed and Sealed this

Twentieth Day of November, 2007

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 7,202,271 B2 |
| APPLICATION NO. | : 10/945471 |
| DATED | : April 10, 2007 |
| INVENTOR(S) | : Daniel G. Baden et al. |

It is certified that error appears in the above-identified patent and that said Letters Patent is hereby corrected as shown below:

In the Specification

Column 1, Line 6, insert the following:
--"This invention was made with government support under ES010594 awarded by the National Institutes of Health. The government has certain rights in the invention."--

Signed and Sealed this
Fourteenth Day of February, 2023

Katherine Kelly Vidal
*Director of the United States Patent and Trademark Office*